US009221055B2

(12) United States Patent
Shoji et al.

(10) Patent No.: US 9,221,055 B2
(45) Date of Patent: Dec. 29, 2015

(54) REACTION PLATE ASSEMBLY, REACTION PLATE AND NUCLEIC ACID ANALYSIS DEVICE

(75) Inventors: Yasunori Shoji, Hitachinaka (JP); Muneo Maeshima, Mito (JP); Chihiro Uematsu, Kawasaki (JP); Makiko Takahashi, Hitachinaka (JP); Kyoko Imai, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 285 days.

(21) Appl. No.: 13/883,830

(22) PCT Filed: Oct. 27, 2011

(86) PCT No.: PCT/JP2011/074767
§ 371 (c)(1),
(2), (4) Date: May 7, 2013

(87) PCT Pub. No.: WO2012/063647
PCT Pub. Date: May 18, 2012

(65) Prior Publication Data
US 2013/0230908 A1 Sep. 5, 2013

(30) Foreign Application Priority Data

Nov. 8, 2010 (JP) ................................ 2010-249275
Nov. 8, 2010 (JP) ................................ 2010-249365

(51) Int. Cl.
*C12M 3/00* (2006.01)
*C12M 1/34* (2006.01)
(Continued)

(52) U.S. Cl.
CPC ............... *B01L 7/52* (2013.01); *B01L 3/50851* (2013.01); *B01L 3/50855* (2013.01);
(Continued)

(58) Field of Classification Search
CPC .................. B01L 2200/025; B01L 2300/0803; B01L 2300/0822; B01L 3/50851; B01L 3/50855; B01L 7/52; B01L 7/5255; B01L 7/00; G01N 2035/00366; G01N 2035/0429; G01N 2035/0441; G01N 2035/0465; G01N 21/6456; G01N 21/6486; G01N 35/028; G01N 35/00

USPC ...................... 435/287.2, 287.1, 287.3, 305.1
See application file for complete search history.

(56) References Cited

U.S. PATENT DOCUMENTS

| 4,635,985 A | * | 1/1987 | Rooke | .................. | B25J 15/0052 294/119.1 |
| 4,890,175 A | * | 12/1989 | Tezuka | .................. | G11B 17/032 360/86 |

(Continued)

FOREIGN PATENT DOCUMENTS

| JP | 61-274267 | 12/1986 |
| JP | 11-326339 | 11/1999 |

(Continued)

OTHER PUBLICATIONS

English translation of Onoe (JP2008-185389-submitted on IDS).*
(Continued)

*Primary Examiner* — Michael Marcheschi
*Assistant Examiner* — Shanta G Doe
(74) *Attorney, Agent, or Firm* — Baker Botts L.L.P.

(57) ABSTRACT

Nucleic acid analysis apparatus includes a plurality of temperature adjustment apparatuses, a rotating mechanism, a delivery base and an ejection base, a delivery drive mechanism, an ejection drive mechanism, and a detection apparatus. The rotating mechanism can include a rotating shaft and a plurality of pressing portions that rotate around the rotating shaft. The reaction plate assembly can move over the temperature adjustment apparatuses along the circumferential direction in a state of being pressed onto the temperature adjustment apparatuses by the pressing portions. The delivery drive mechanism can cause the reaction plate assembly to be moved radially inward and delivered between the pressing portions and temperature adjustment apparatuses. The ejection drive mechanism can cause the reaction plate assembly to be moved radially outward and ejected from between the pressing portions and temperature adjustment apparatuses onto the ejection base. Reaction plates, reaction plate assemblies, and nucleic acid analysis apparatuses are provided.

15 Claims, 16 Drawing Sheets

(51) Int. Cl.
*B01L 7/00* (2006.01)
*G01N 35/02* (2006.01)
*B01L 3/00* (2006.01)
*G01N 21/64* (2006.01)
*G01N 35/00* (2006.01)
*G01N 35/04* (2006.01)

(52) U.S. Cl.
CPC ......... *B01L 7/5255* (2013.01); *G01N 21/6456* (2013.01); *G01N 21/6486* (2013.01); *G01N 35/028* (2013.01); *B01L 2200/025* (2013.01); *B01L 2300/0803* (2013.01); *B01L 2300/0822* (2013.01); *G01N 2035/00366* (2013.01); *G01N 2035/0429* (2013.01); *G01N 2035/0441* (2013.01); *G01N 2035/0465* (2013.01)

(56) References Cited

U.S. PATENT DOCUMENTS

| | | | |
|---|---|---|---|
| 6,908,594 | B1 | 6/2005 | Schaevitz et al. |
| 2002/0001848 | A1* | 1/2002 | Bedingham et al. ............ 436/45 |
| 2003/0032191 | A1* | 2/2003 | Hilson ............. G01N 35/00029 436/47 |
| 2004/0231870 | A1* | 11/2004 | McCormick ............. B25B 5/12 173/217 |
| 2005/0239119 | A1 | 10/2005 | Tsukada |
| 2006/0231027 | A1* | 10/2006 | Iwabuchi ............ C23C 16/4586 118/719 |
| 2007/0264164 | A1 | 11/2007 | Hochstrasser et al. |
| 2009/0068064 | A1 | 3/2009 | Gordon |
| 2010/0028124 | A1* | 2/2010 | Lackner ............ G01N 35/0099 414/806 |
| 2010/0086990 | A1 | 4/2010 | Stanley et al. |
| 2010/0279392 | A1* | 11/2010 | Kodama et al. ............ 435/286.1 |

FOREIGN PATENT DOCUMENTS

| | | |
|---|---|---|
| JP | 2004-500233 | 1/2004 |
| JP | 2004-212359 | 7/2004 |
| JP | 2004-536291 | 12/2004 |
| JP | 2005-304445 | 11/2005 |
| JP | 2007-316064 | 12/2007 |
| JP | 2008-185389 | 8/2008 |
| JP | 2010-519892 | 6/2010 |
| KR | 10-2010-0008476 | 1/2010 |
| WO | WO 2008/146754 A1 | 12/2008 |

OTHER PUBLICATIONS

Office Action in JP 2010-249275, dated May 7, 2014, (in Japanese, 3 pgs.), [partial English language translation, 3 pgs.].

Tsuguto Fujimoto et al, Novel High-Speed Real-Time PCR Method (Hyper-PCR): Results from Its Application to Adenovirus Diagnosis, Jpn. J. Infect. Dis., 63, 2010, pp. 31-35.

Tsuguto Fujimoto, Diagnosis of Adenovirus with High-Speed PCR System, Clinical Study and Microorganisms May 2009, vol. 36, No. 3.

Office Action in JP 2010-249365, dated May 7, 2014, (in Japanese, 2 pgs.), [partial English language translation, 2 pgs.].

* cited by examiner

REACTION PLATE ASSEMBLY, REACTION PLATE AND NUCLEIC ACID ANALYSIS DEVICE

TECHNICAL FIELD

The present invention relates to a nucleic acid analysis apparatus for analyzing a biological sample by amplifying a nucleic acid contained in the biological sample.

BACKGROUND ART

Analysis of nucleic acids contained in biological samples, such as blood, plasma, and tissue fragment, is conducted in various fields, including not just academic researches such as biology, biochemistry, and medicine, but also industries for diagnosis, breed improvement for agricultural crops, and food inspection. One of the most widely employed methods for analyzing nucleic acids is PCR (Polymerase Chain Reaction), which is a technology for amplifying a nucleic acid in a region to be analyzed in a base sequence-specific manner. In an application of PCR, a fluorescence label may be attached to the nucleic acid to be analyzed and then irradiated with excitation light to measure fluorescent intensity over time, so that trace amounts of the nucleic acid can be detected with high sensitivity.

In PCR, a solution containing a nucleic acid and a reagent for amplifying the nucleic acid is heated to approximately 95° C. so as to thermally denature the nucleic acid, which is then cooled to approximately 60° C. such that annealing and elongation of the nucleic acid can take place, and this cycle may be repeated 30 to 40 times. In a currently mainstream PCR apparatus, a reaction plate referred to as a "microtiter plate" with 96 to 386 reaction wells is disposed on a Peltier element, and the temperature of the Peltier element is increased and decreased so as to provide a temperature cycle. In this method, however, it takes time to cause a temperature change in the Peltier element itself, posing a problem in decreasing analysis time.

Further, in the above method, a batch process such that a plurality of samples set in the 96 to 386 reaction wells is processed all at once is inevitable. Once a process is started, the next process cannot be started until the first batch is completed.

Non-patent Document 1 discloses a structure such that, in order to solve the problem of increasing the speed of the temperature cycle, a disc-shaped reaction plate with reaction wells is rotated over and in contact with heaters set for a plurality of temperatures in advance. In this example, the need for changing the temperature of the heater is eliminated, so that the temperature of the reaction plate can be changed quickly. Further, in order to facilitate the reception of heat from a temperature adjustment apparatus disposed on an upper side or a lower side, measures are taken to expand a sample solution in a planar direction.

Patent Document 1: JP Patent Publication (Kokai) No. 2008-185389 A
Patent Document 2: U.S. Patent Publication No. 2009/0068064 A1
Non-patent Document: Tsuguto Fujimoto, et al., Jpn. J. Infect. Dis., 63, 31-35 (2010)

SUMMARY OF THE INVENTION

Problem to be Solved by the Invention

Patent Document 1 describes an example of a temperature control apparatus provided with a mechanism for rotating a disc-shaped microchip with a plurality of wells. Patent Document 2 describes an apparatus such that a fan-shaped plate insert is loaded on a disc assay plate.

In a conventional nucleic acid analysis apparatus, the analysis of a loaded reaction plate has to be completed before the next reaction plate can be loaded. Further, the reaction plate cannot be loaded as needed, and the reaction plate cannot be unloaded as needed. The conventional nucleic acid analysis apparatus does not have a high degree of freedom in loading or unloading the reaction plate, so that an efficient nucleic acid analysis cannot be performed.

An object of the present invention is to provide a technology such that, in nucleic acid analysis, a high degree of freedom in loading or unloading a reaction plate can be obtained and efficient sample analysis can be performed.

Means for Solving the Problem

According to the present invention, a reaction plate assembly includes a reaction plate with one or more reaction wells; a visible light transmissive cover mounted on the reaction plate and covering the reaction wells; and a visible light transmissive weight member covering the cover. The reaction wells are disposed in an arc shape along the circumference of a circle with a predetermined radius r1.

According to the present invention, a nucleic acid analysis apparatus includes a plurality of temperature adjustment apparatuses disposed along a circumferential direction; a rotating mechanism that rotates a reaction plate assembly disposed over the temperature adjustment apparatuses along the circumferential direction; a delivery base and an ejection base which are installed on an outer peripheral side of the temperature adjustment apparatuses; a delivery drive mechanism that delivers the reaction plate assembly from the delivery base onto the temperature adjustment apparatuses; an ejection drive mechanism that ejects the reaction plate assembly from the temperature adjustment apparatuses to the ejection base; and a detection apparatus that optically detects a sample loaded on the reaction plate assembly.

According to the present invention, the rotating mechanism includes a rotating shaft and a plurality of pressing portions that rotate about the rotating shaft. The reaction plate assembly is configured to be moved in the circumferential direction over the temperature adjustment apparatuses in a state of being pressed onto the temperature adjustment apparatuses by the pressing portions.

The delivery drive mechanism may cause the reaction plate assembly disposed on the delivery base to be moved radially inward and delivered between the pressing portions and the temperature adjustment apparatuses.

The ejection drive mechanism may cause the reaction plate assembly disposed over the temperature adjustment apparatuses to be moved radially outward and ejected from between the pressing portions and the temperature adjustment apparatuses onto the ejection base.

Effects of the Invention

According to the present invention, a technology such that, in nucleic acid analysis, a high degree of freedom in loading or unloading a reaction plate can be obtained and a sample can be efficiently analyzed is provided.

MODE FOR CARRYING OUT THE INVENTION

Figure 1:
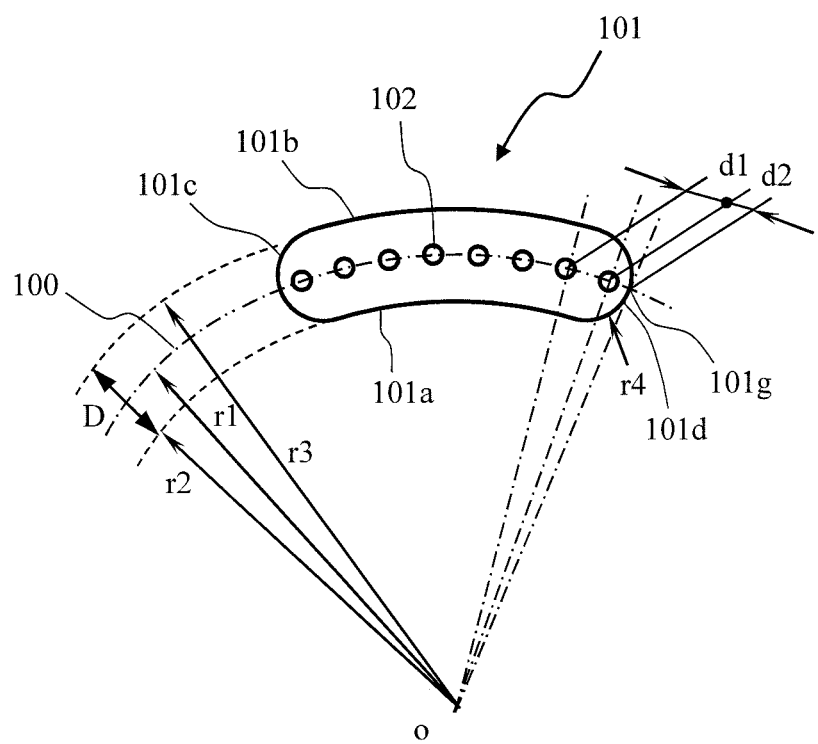
FIG. 1 is a plan view of a first embodiment of a reaction plate according to the present invention.

FIG. 1 is a plan view of a first embodiment of a reaction plate according to the present invention. The reaction plate 101 includes a plurality of reaction wells 102 formed therein. While in the present example the number of the reaction wells 102 is eight, the number of the reactions wells 102 may be greater or smaller. While in the present example the reaction wells 102 have a circular planar shape, the reaction wells 102 may have an elliptical, square, or polygonal planar shape. The reaction wells 102 are formed along a circumference 100 at a radius r1 from the center o. In the present example, any two adjacent reaction wells 102 have a constant interval d1 between the centers thereof. This is because in a nucleic acid analysis apparatus, the constant interval d1 facilitates the signal processing during the measurement of fluorescent intensity from the reaction wells 102. The interval d1, however, may not be constant.

The reaction plate 101 is formed in a band-like arc shape with a width D. The outer shape of the reaction plate 101 is defined by a boundary 101$a$ on the inner peripheral side, a boundary 101$b$ on the outer peripheral side, and semicircular boundaries 101$c$ and 101$d$ at both ends. The boundary 101$a$ on the inner peripheral side is a part of a circumference with a radius r2 from the center o. The boundary 101$b$ on the outer peripheral side is a part of a circumference with a radius r3 from the center o. The semicircular boundaries 101$c$ and 101$d$ at the ends are each a part of a circumference with a radius r4 from a center on the circumference 100. The width D of the reaction plate 101 is D=r3−r2. Preferably, the reaction wells 102 are disposed at the center of the width D of the reaction plate 101. In this case, r3−r1=r1−r2=D/2. The semicircular boundaries 101$c$ and 101$d$ at the ends each may be a part of the circumference with the radius D/2. In this case, r4=D/2.

When a plurality of the reaction plates 101 is arranged along the circumference 100, all of the reaction wells are preferably disposed at the equal intervals d1. Further, a slight gap is preferably provided between two adjacent reaction plates 101. A condition for this purpose will be described. Let the intersection point of the right-side semicircular boundary 101$d$ and the circumference 100 be 101$g$. Let the distance between the center of the extreme-right one of the reaction wells of the reaction plate 101 and the intersection point 101$g$ be d2. Then, by setting d2 to be not more than one half d1, all of the reaction wells can be disposed at the equal intervals d1 when the plurality of the reaction plates 101 is arranged along the circumferential direction. The same applies to the distance between the left-side semicircular boundary 101d and the extreme-left reaction well.

Figure 2:
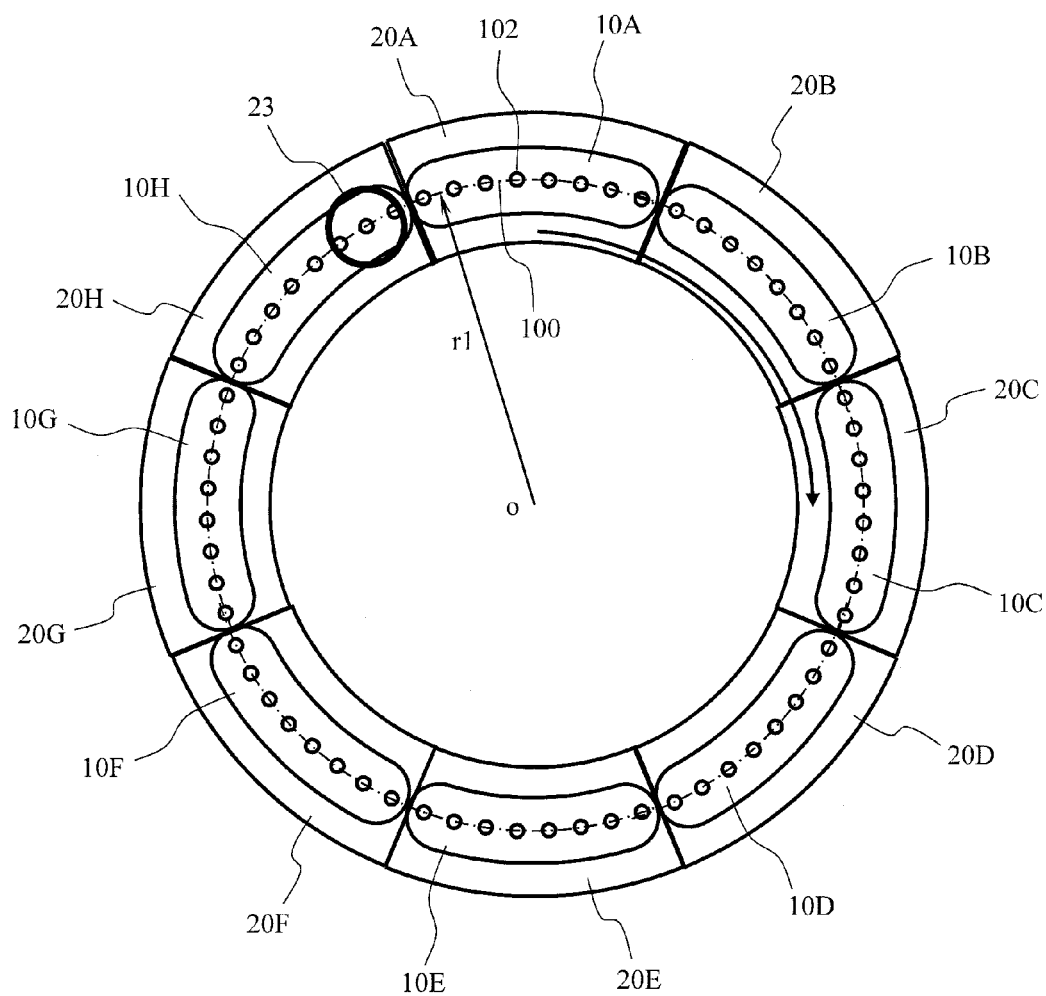
FIG. 2 illustrates an example of a method for loading the reaction plate according to the present invention in a nucleic acid analysis apparatus.

FIG. 2 schematically illustrates a planar configuration of a nucleic acid analysis apparatus according to the present invention. The nucleic acid analysis apparatus of the present example is configured such that PCR can be performed. The nucleic acid analysis apparatus of the present example includes eight temperature adjustment apparatuses 20A to 20H disposed along the circumference. Over the eight temperature adjustment apparatuses 20A to 20H, eight reaction plate assemblies 10A to 10H are disposed. Each of the reaction plate assemblies 10A to 10H includes a reaction plate, a transparent cover disposed over the reaction plate, and further a transparent weight member disposed over the transparent cover. In the present example, the transparent cover and the transparent weight member are not illustrated. The reaction wells 102 disposed on the reaction plate are illustrated. Instead of the reaction plate assemblies 10A to 10H, the reaction plates may be directly disposed over the temperature adjustment apparatuses 20A to 20H.

The eight temperature adjustment apparatuses 20A to 20H may have the same shape and size. The shape and size of the temperature adjustment apparatuses and the shape and size of the reaction plate assemblies 10A to 1014 are matched with each other. For example, the size of the reaction plate assemblies 10A to 10H in the circumferential direction is matched with the size of the temperature adjustment apparatuses 20A to 20H in the circumferential direction. Namely, the size of the reaction plate assemblies 10A to 10H in the circumferential direction is the same as, or slightly smaller than, the size of the temperature adjustment apparatuses 20A to 20H in the circumferential direction.

As illustrated, the reaction plate assemblies 10A to 10H are disposed over the temperature adjustment apparatuses such that the plurality of reaction wells 102 is disposed in a row along the circumference 100 with the radius r1 from the center o. All of the reaction wells 102 are disposed at equal intervals along the circumference 100 with the radius r1 from the center o.

The reaction plate assemblies 10A to 10H are moved over the eight temperature adjustment apparatuses at a predetermined speed by a rotating mechanism which is not illustrated. When the reaction plate assemblies are moved over the temperature adjustment apparatuses along the circumferential direction, all of the reaction wells are moved along the circumference 100 with the radius r1 at the predetermined speed. While the reaction plate assemblies 10A to 1011 are moved over the temperature adjustment apparatuses, the reaction plates are in thermal contact with the temperature adjustment apparatuses. Thus, the reaction plates are maintained at a desired temperature by the temperature adjustment apparatuses.

The nucleic acid analysis apparatus according to the present example is provided with a delivery drive mechanism that delivers the reaction plate assemblies onto the temperature adjustment apparatuses, and an ejection drive mechanism that ejects the reaction plate assemblies from the top of the temperature adjustment apparatuses. The delivery drive mechanism and the ejection drive mechanism are configured to deliver and eject the reaction plate assemblies along the radial direction. In the nucleic acid analysis apparatus according to the present example, the reaction plate assemblies are disposed over the eight temperature adjustment apparatuses. Thus, the delivery drive mechanism and the ejection drive mechanism can perform delivery and ejection of the reaction plate assemblies without stopping the rotation of the rotating mechanism.

Above the eighth temperature adjustment apparatus 20H, a detection apparatus 23 is disposed. The detection apparatus 23 may be an optical inspection apparatus that irradiates the reaction wells 102 with excitation light and measures the intensity of fluorescence from the reaction wells 102. By providing a plurality of the detection apparatuses 23, emission from a plurality of dyes may be detected.

When the reaction plate assemblies slide over the eighth temperature adjustment apparatus 20H, the plurality of reaction wells of the reaction plate assemblies pass immediately below the detection apparatus 23. Specifically, a detector unit of the detection apparatus 23 may be disposed on the circumference 100 with the radius r1 such that the plurality of reaction wells of the reaction plate assemblies can be optically detected.

Because all of the reaction wells 102 pass under the detection apparatus 23, fluorescent intensity measurement can be performed for all of the reaction wells 102 without moving the detection apparatus 23. Even during the rotation of the rotating mechanism, the position of the inspection portion of the detection apparatus 23 and the position of the reaction wells 102 on the reaction plate are aligned. In the nucleic acid analysis apparatus according to the present example, the sample loaded in the reaction wells 102 can be optically detected by the detection apparatus 23 without stopping the rotation of the rotating mechanism.

The eight temperature adjustment apparatuses 20A to 20H are independently temperature-controlled. Specifically, the temperature of the eight temperature adjustment apparatuses 20A to 20H is adjusted independently according to a predetermined temperature cycle. For example, a temperature setting is made such that one temperature cycle for PCR is implemented when each of the reaction plate assemblies 10A to 10H makes a circuit along the circumferential direction over the eight temperature adjustment apparatuses 20A to 20H. For example, the temperature of the first and the second temperature adjustment apparatus 20A and 20B is set for 95° C., and the temperature of the third to the eighth temperature adjustment apparatus 20C to 20H is set for 60° C. While the reaction plate assemblies are moved over the first and the second temperature adjustment apparatus 20A and 20B, the nucleic acid is thermally denatured. While the reaction plate assemblies are moved over the third to the eighth temperature adjustment apparatus 20C to 20H, annealing and elongation of the nucleic acid proceed.

Figure 3:
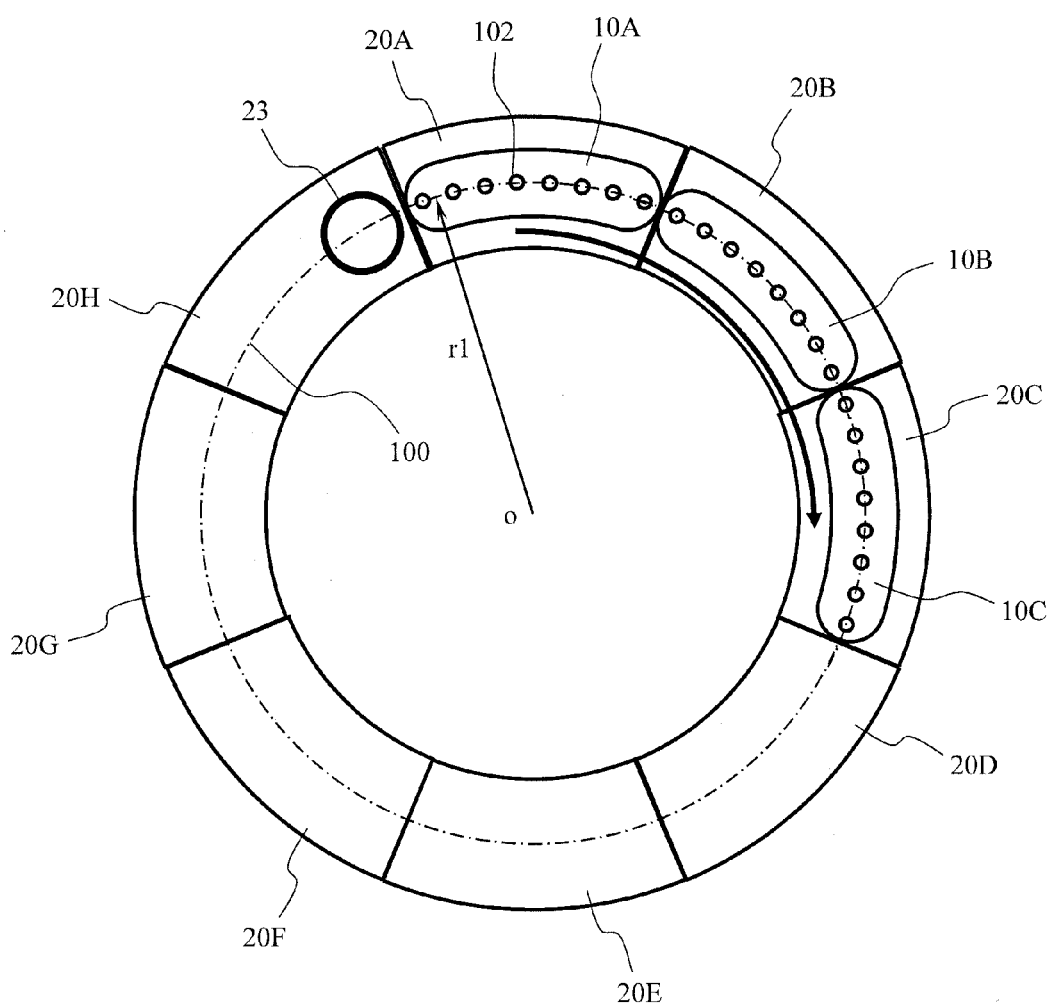
FIG. 3 illustrates another example of the method for loading the reaction plate according to the present invention in the nucleic acid analysis apparatus.

With reference to FIG. 3, in the present example, three reaction plate assemblies 10A to 10C are loaded on the eight temperature adjustment apparatuses 20A to 20H. In the illustrated example, the three reaction plate assemblies 10A to 10C are disposed adjacent to each other. However, the three reaction plate assemblies 10A to 10C may be spaced apart from each other. In the nucleic acid analysis apparatus according to the present example, any number of the reaction plate assemblies 10A to 10C can be loaded as long as the number is not more than eight.

After a PCR (Polymerase Chain Reaction) is started, it is necessary to repeat the temperature cycle 30 to 40 times for the three reaction plate assemblies 10A to 10C. According to the present example, five other reaction plate assemblies can be added. For example, after the three reaction plate assemblies 10A to 10C have been subjected to the temperature cycle, it may be desired to perform a further analysis for another sample. In such a case, a reaction plate assembly may be added. The reaction plate assembly for which the temperature cycle has been completed a predetermined number of times may be ejected as needed.

In the nucleic acid analysis apparatus according to the present example, the number of the reaction plate assemblies 10A to 10C can be freely changed depending on the number of the samples to be analyzed. Thus, compared with the conventional technology in which a plurality of samples is batch-processed by using a disc-type reaction plate, wasteful use of the reaction plate can be reduced. The nucleic acid analysis apparatus according to the present example eliminates the inconvenience of having to wait until an analysis is completed before the next analysis can be started. Accordingly, the unwanted standby time can be eliminated.

In the nucleic acid analysis apparatus according to the present example, compared with the conventional technology, the advantage of a higher degree of freedom in loading or unloading the reaction plate can be obtained, as will be described below.

In the nucleic acid analysis apparatus according to the present example, the reaction plate assemblies or the reaction plates are disposed over the eight temperature adjustment apparatuses. Thus, the delivery drive mechanism and the ejection drive mechanism can perform the delivery and ejection of the reaction plate assemblies or the reaction plates without stopping the rotation of the rotating mechanism. Further, in the reaction plate assemblies or the reaction plates of the present example, the reaction wells 102 are disposed along the circumference. Thus, the sample in the reaction wells 102 can be optically detected by the detection apparatus 23 without stopping the rotating mechanism. Namely, in the nucleic acid analysis apparatus according to the present example, the reaction plate assemblies or the reaction plates can be rotated at a constant speed at all times without stopping the rotating mechanism. Accordingly, when the reaction plate assemblies or the reaction plates are loaded successively or as needed, the same temperature cycle can be implemented. In this way, according to the present invention, the reaction plate assemblies or the reaction plates can be loaded successively or as needed.

Figure 4:
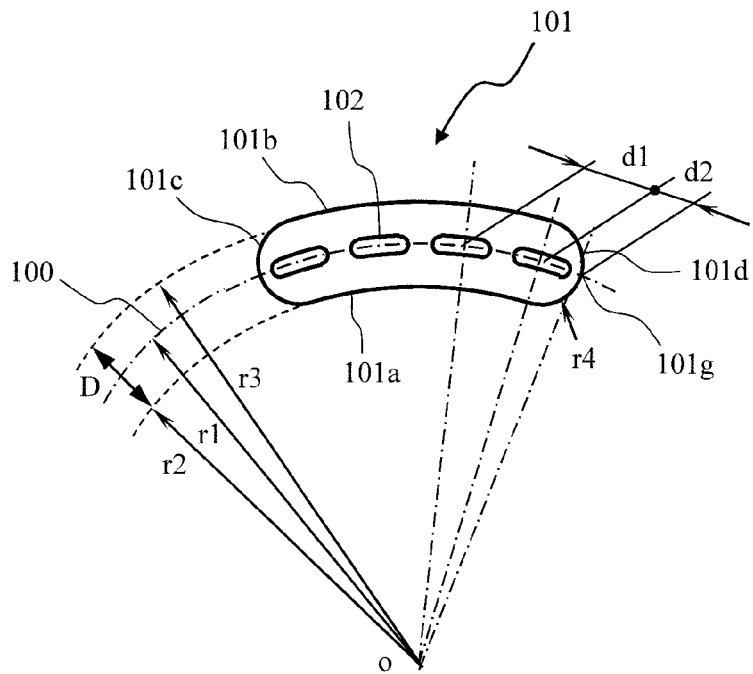
FIG. 4 is a plan view of a second embodiment of the reaction plate according to the present invention.

FIG. 4 is a plan view of a second embodiment of the reaction plate according to the present invention. In the reaction plate according to the present example, the reaction wells 102 have an arched oblong planar shape. The reaction wells 102 may have an arched rectangular or thin polygonal planar shape. The diameter of the oblong in the longitudinal direction extends along the circumference 100 with the radius r1 from the center o. The reaction plate according to the present example may be similar to the first embodiment of FIG. 1 with the exception that the shape of the reaction wells is oblong. For example, the interval d1 between the centers of any two adjacent reaction wells 102 may be constant.

Preferably, when a plurality of the reaction plates 101 is arranged along the circumference 100, all of the reaction wells are disposed at the equal intervals d1. Preferably, a slight gap is provided between any two adjacent reaction plates 101. A condition for this purpose will be described. Let the intersection point of the right-side semicircular boundary 101d and the circumference 100 be 101g. Let the distance between the center of the extreme-right one of the reaction wells of the reaction plate 101 and the intersection point 101g be d2. Then, by setting d2 to be not more than one half d1, all of the reaction wells can be disposed at the equal intervals d1 when the plurality of the reaction plates 101 is arranged along the circumferential direction. The same applies to the distance between the left-side semicircular boundary 101c and the extreme-left reaction well.

In the reaction plate 101 according to the present example, because the reaction wells 102 have the thin arc shape, the reaction wells 102 take a relatively long time before passing the detection apparatus 23. Thus, the time for the detection apparatus 23 to observe the individual reaction wells 102 is extended. Accordingly, the accuracy of detection by the detection apparatus 23 can be increased.

Figure 5:
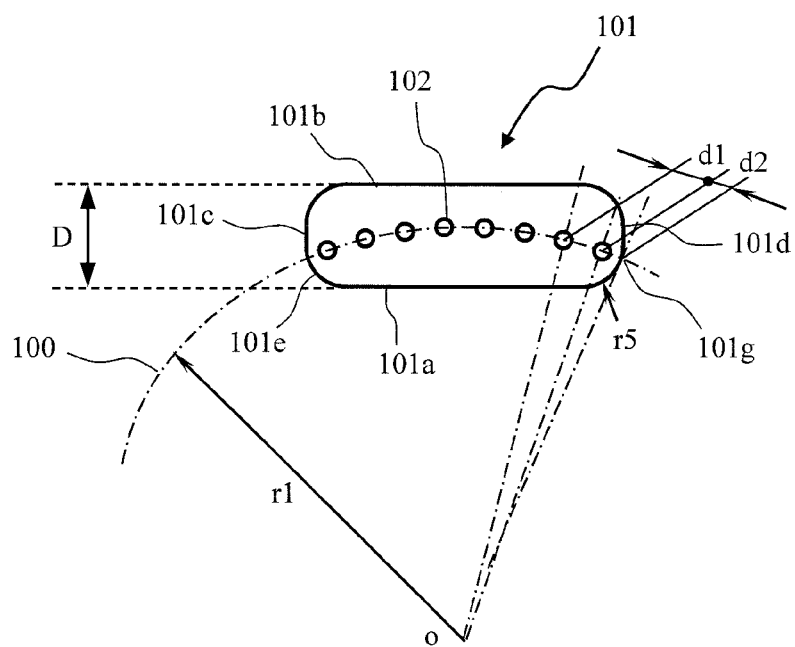
FIG. 5 is a plan view of a third embodiment of the reaction plate according to the present invention.

FIG. 5 is a plan view of a third embodiment of the reaction plate according to present invention. The reaction plate 101 according to the present example has a linear band-like shape with the width D. The reaction plate 101 is a rectangle with the rounded corners. The outer shape of the reaction plate 101 is defined by the inner boundary 101a, the outer boundary 101b, and the linear boundaries 101c and 101d at the ends. The four rounded corners are each a part of a circumference with a radius r5. The linear boundaries 101c and 101d at the ends may be replaced with the semicircular boundaries 101c and 101d according to the first embodiment illustrated in FIG. 1.

While in the present example the reaction wells 102 have a circular planar shape, the reaction wells 102 may have an elliptical, square, or polygonal planar shape. The reaction wells 102 are formed along the circumference 100 with the radius r1 from the center o. Preferably, in the present example, the interval d1 between the centers of any two adjacent reaction wells 102 is constant.

Preferably, when a plurality of the reaction plates 101 is arranged along the circumference 100, all of the reaction wells are disposed at the equal intervals d1. Preferably, a slight gap is provided between any two adjacent reaction plates 101. A condition for this purpose will be described. Let the intersection point of the right-side semicircular boundary 101d and the circumference 100 be 101g. Let the distance between the center of the extreme-right one of the reaction wells of the reaction plate 101 and the intersection point 101g be d2. Then, by setting d2 to be not more than one half d1, all of the reaction wells can be disposed at the equal intervals d1 when the plurality of the reaction plates 101 is arranged along the circumferential direction. The same applies to the distance between the left-side semicircular boundary 101c and the extreme-left reaction well.

Figure 6:
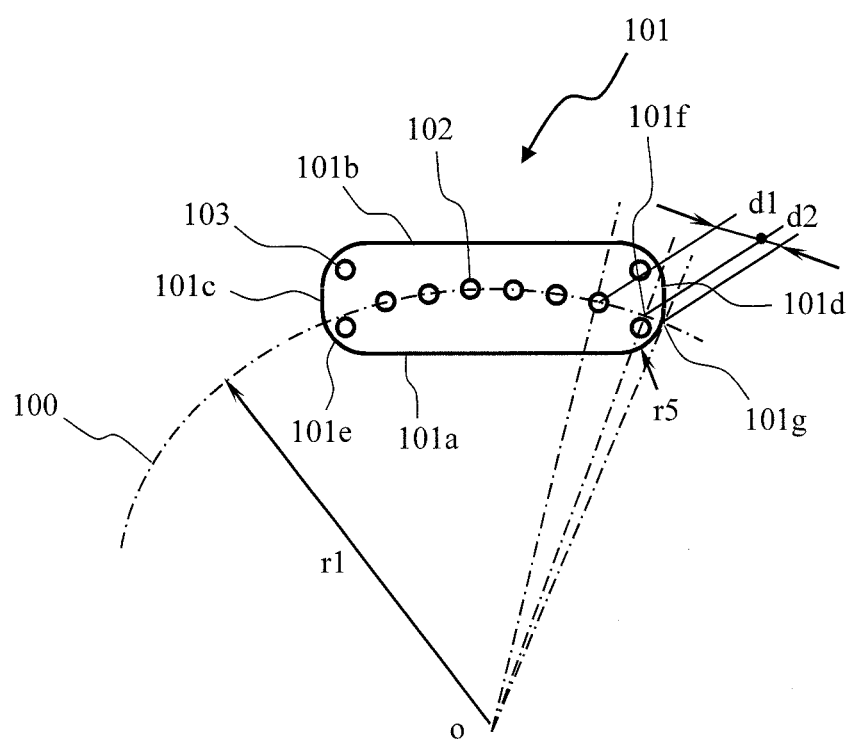
FIG. 6 is a plan view of a fourth embodiment of the reaction plate according to the present invention.

FIG. 6 is a plan view of a fourth embodiment of the reaction plate according to the present invention. While the basic structure is the same as the third embodiment illustrated in FIG. 5, the reaction wells at the ends are not provided in the present example. For example, the reaction well that is supposed to be disposed at an extreme-right position 101f is omitted. Instead, two holes 103 are formed at each end. While in the present example the number of the holes 103 is four, the number may be greater or smaller. Further, while in the present example the holes 103 have a circular planar shape, the holes 103 may have a polygonal planar shape. The holes 103 may be either through holes or non-through holes, i.e., holes with a bottom. The function of the holes 103 will be described later.

In the present example, too, the interval d1 between the centers of any two adjacent reaction wells 102 on the reaction plate 101 may be constant.

Preferably, when a plurality of the reaction plates 101 is arranged along the circumference 100, all of the reaction wells are disposed at the equal intervals d1. However, in the present example, because the reaction wells at the ends are omitted, not all of the reaction wells can be disposed at the equal intervals d1 when the plurality of the reaction plates 101 is arranged along the circumference 100. However, signal processing may be facilitated by storing the positional information about the missing reaction wells.

Further, preferably, a slight gap is provided between any two adjacent reaction plates 101 when a plurality of the reaction plates 101 is arranged along the circumference 100. A condition for that purpose will be described. Let the intersection point of the right-side semicircular boundary 101d and the circumference 100 be 101g. Let the distance between the position 101f of the extreme-right reaction well that is omitted and the point 101g be d2. Then, by setting d2 to be not more than one half d1, any two adjacent reaction plates 101 do not interfere with each other when the plurality of the reaction plates 101 is arranged along the circumferential direction. The interval between the reaction wells at the ends of the two adjacent reaction plates 101 may be twice d1. The same applies to the distance between the left-side semicircular boundary 101c and the extreme-left reaction well.

In the present example, because of the holes 103 formed at the ends of the reaction wells, no reaction well can be formed at the extreme-right position 101f and the corresponding extreme-left position on the circumference 100. However, by moving the position of the holes 103 to other positions, or omitting those of the two sets of holes that are on the inner peripheral side, reaction wells may be provided at the extreme right position 101f and the corresponding position on the left end.

Further, the holes 103 may be provided at or around the center of the reaction plate 101, rather than at the ends thereof.

Figure 7A:
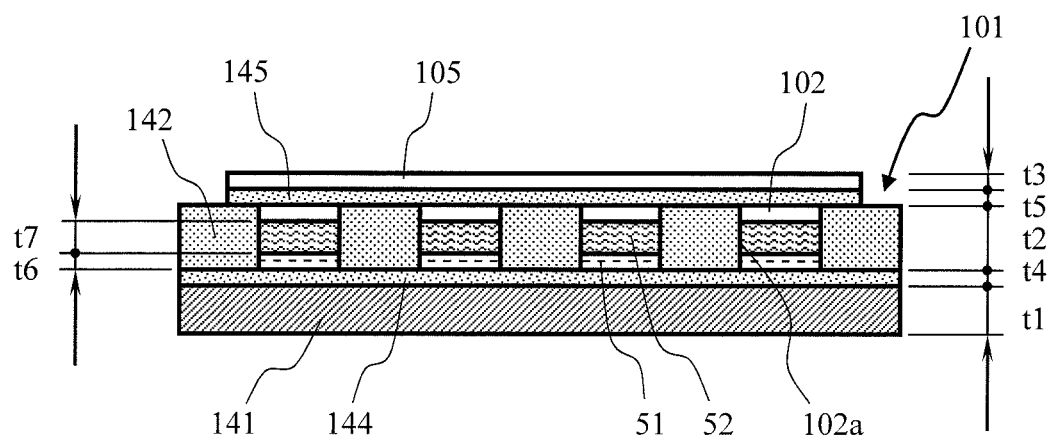
FIG. 7A illustrates a cross sectional configuration of the reaction plate according to the present invention.
Figure 7B:
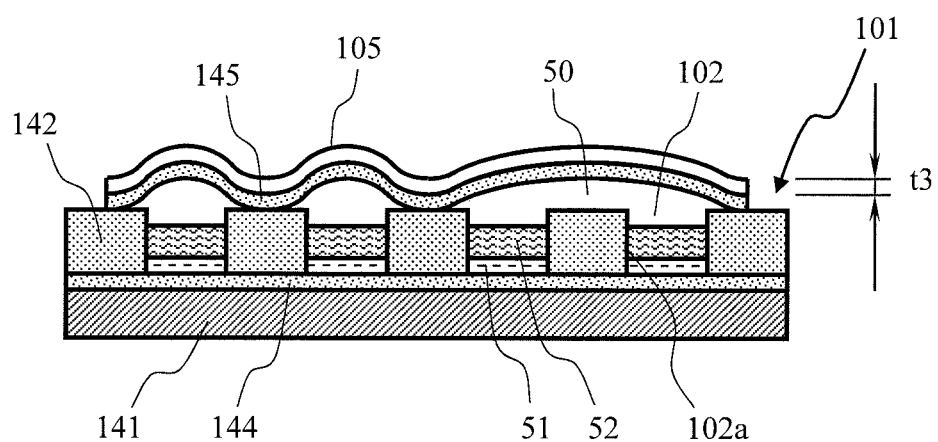
FIG. 7B is a cross sectional view illustrating the behavior of the reaction plate according to the present invention during an increase in temperature.

With reference to FIGS. 7A and 7B, an example of the cross sectional structure of the reaction plate according to the present invention will be described. As illustrated in FIG. 7A, the reaction plate 101 includes a bottom plate portion 141 and a main plate portion 142 disposed thereon. On the reaction plate 101, a cover 105 is attached. The bottom plate portion 141 and the main plate portion 142 are affixed to each other by an adhesive layer 144 disposed therebetween. The main plate portion 142 and the cover 105 are affixed to each other by an adhesive layer 145 disposed therebetween.

When the bottom plate portion 141 and the main plate portion 142 are of such material that they can directly adhere to each other, the adhesive layer 144 may be omitted. When the main plate portion 142 and the cover 105 are of such material that they can directly adhere to each other, the adhesive layer 145 may be omitted.

In the upper surface of the reaction plate 101, the reaction wells 102 are provided. Side walls 102a of the reaction wells 102 are formed by the inner surfaces of through holes formed in the main plate portion 142. The bottom of the reaction wells 102 is formed by the upper surface of the bottom plate portion 141. In the reaction wells 102, a sample solution 51 is placed and then oil 52 is placed thereon. Further, the cover 105 is attached to the upper surface of the main plate portion 142 so as to prevent evaporation. The oil 52 is used for preventing evaporation of the sample solution 51 until the cover 105 is attached. The oil 52 may not be used when the cover 105 can be attached in a short time after the sample solution 51 is placed in the reaction wells 102.

The thickness of the bottom plate portion 141, the main plate portion 142, and the cover 105 is t1, t2, and t3, respectively. The thickness of the adhesive layers 144 and 145 is t4 and t5, respectively. The height of the sample solution 51 and the oil 52 is t6 and t7, respectively.

In the present example, the detection apparatus 23 for detecting fluorescence is disposed above the reaction plate 101. Fluorescence from the sample solution 51 in the reaction wells 102 passes through the cover 105 and the adhesive layer 145. Thus, the cover 105 and the adhesive layer 145 are formed from a material that transmits visible light. The cover 105 and the adhesive layer 145 may include an adhesive polypropylene sheet provided with an adhesive layer in advance. The thickness t3 and t5 of the cover 105 and the adhesive layer 145 may be minimized such that the fluorescence is not attenuated.

In the present example, the reaction plate 101 is disposed over the temperature adjustment apparatuses. The heat from the temperature adjustment apparatuses is transmitted mainly from the lower surface of the reaction plate 101 to the sample solution 51 in the reaction wells 102 via the bottom plate portion 141. Thus, the bottom plate portion 141 is preferably formed from a material with large heat conductivity. Generally, a resin such as polypropylene is often used for the reaction plate 101 for nucleic acid analysis. However, resins have a relatively small heat conductivity. Thus, preferably, a metal with a relatively large heat conductivity may be used for the bottom plate portion 141. Further preferably, metals with particularly high heat conductivity, such as silver, copper, gold, or aluminum may be used. In order to avoid thermal loss as much as possible and improve response to heating, the heat conduction path between the temperature adjustment apparatuses and the reaction wells may be decreased. For this purpose, the thickness t1 of the bottom plate portion 141 may be minimized.

When a metal is used for the bottom plate portion 141, the sample may possibly be contaminated. In such a case, the adhesive layer 144 may be provided with the function of a passivation layer. For example, a silicone material-based adhesive may be used. Preferably, in this case, too, the thickness t4 of the adhesive layer 144 is minimized so as to decrease the length of the heat conduction path between the temperature adjustment apparatuses and the reaction wells.

For the main plate portion 142, various materials may be used. For example, a resin such as polypropylene, which is generally used for nucleic acid analysis, may be is used. Some of the heat from the temperature adjustment apparatuses is transmitted via the bottom plate portion 141, the adhesive layer 144, and the main plate portion 142 to the sample solution 51 in the reaction wells 102. Desirably, the heat conduction path should have a short length. Thus, the height t6 and t7 of the sample solution 51 and the oil 52, respectively, may be minimized, and accordingly the thickness t2 of the main plate portion 142 may also be minimized. For example, the thickness t2 of the main plate portion 142 is preferably not more than 1 mm and more preferably not more than 0.5 mm.

By using a material that does not easily transmit visible light for the main plate portion 142, optical interference with the adjacent reaction wells can be blocked. In this way, the S/N ratio of fluorescent intensity measurement can be improved. For example, as the material for the main plate portion 142, a black-colored resin, such as polypropylene, is used.

With reference to FIG. 7B, the behavior of the reaction plate during an increase in temperature will be described. Normally, the cover 105 is attached to the reaction plate 101 at room temperature. The temperature of the reaction plate 101 increases to approximately 95° C. when subjected to a temperature cycle for PCR. Thus, the sample solution 51 vaporizes and the internal pressure of the reaction wells 102 increases. If the cover 105 does not have a sufficient strength, the cover 105 may be deformed by the increase in internal pressure. When the amount of deformation of the cover 105 is increased, the cover 105 may be peeled from the main plate portion 142. Namely, the adhesive layer 145 that adheres the cover 105 onto the main plate portion 142 may be peeled. When the cover 105 is peeled, a communicating portion 50 is produced between the reaction wells. When the communicating portion 50 is produced, contamination may occur between the reaction wells that have been placed in communication with each other, thereby preventing accurate analysis.

In order to prevent the deformation and peeling of the cover 105, the cover 105 may be formed from a high-rigidity material, or the thickness t3 of the cover 105 may be increased. However, this may result in an increase in the production cost for the reaction plate 101. Normally, in the nucleic acid analysis apparatus, the reaction plate 101 that has been used once for analysis is discarded to prevent contamination. Namely, the reaction plate 101 is normally disposable. Thus, measures that would lead to an increase in production cost for the reaction plate 101 is not desirable. In the following, a method for preventing the deformation and peeling of the cover 105 without an increase in production cost for the reaction plate 101 will be described.

Figure 8:
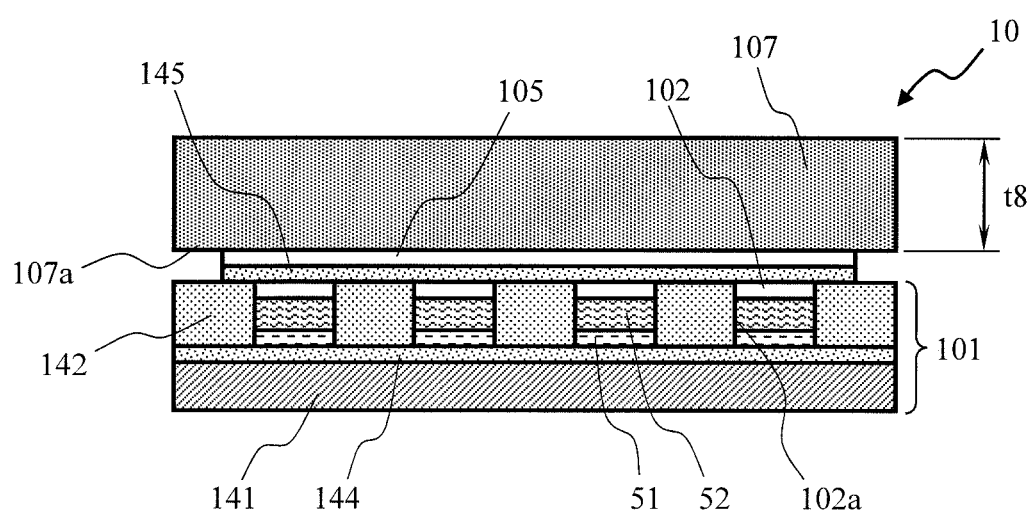
FIG. 8 illustrates a cross sectional configuration of a reaction plate assembly according to the present invention.

FIG. 8 illustrates an example of the structure of the reaction plate assembly according to the present invention. The reaction plate assembly according to the present example includes the reaction plate 101, the cover 105 disposed thereon, and a weight member 107 disposed further thereon. The weight member 107 is disposed on the cover 105 in a detachable manner. Namely, no adhesive is provided between the cover 105 and the weight member 107. The weight member 107 has a thickness t8.

While the reaction plate 101 may be disposable, the weight member 107 may be used repeatedly. As described above, in the present example, the detection apparatus 23 is disposed above the reaction plate 101 to detect fluorescence. Because fluorescence from the sample solution 51 in the reaction wells 102 passes through the weight member 107, the weight member 107 is made of a material that transmits visible light. The weight member 107 needs to be able to resist deformation and lifting even when the internal pressure of the reaction wells 102 is increased. Thus, a preferred material has a high rigidity and a relatively large specific gravity. Examples of such material include quartz and glass.

Quartz and glass generally have high visible light transmittance. Thus, the thickness t8 of the weight member 107 can be relatively increased, although the thickness t8 is subject to constraints, such as the focal distance of the detection apparatus optics. Namely, the strength and weight of the weight member 107 can be relatively increased. Accordingly, by placing the weight member 107 on the reaction plate 101, the deformation and peeling of the cover 105 can be prevented when the internal pressure of the reaction wells 102 is increased by a temperature increase.

According to the present example, the reaction plate 101 and the cover 105 form a structure of three mutually different layers stacked upon one another. Thus, when the structure is heated by the temperature adjustment apparatuses, the reaction plate 101 may be warped by a bimetallic effect due to the difference in temperature expansion coefficients. By placing the weight member 107 on the reaction plate 101, the warping of the reaction plate 101 can be suppressed and the degree of adhesion between the reaction plate 101 and the temperature adjustment apparatuses can be increased. In this way, the heat transfer rate between the reaction plate 101 and the temperature adjustment apparatuses can be improved.

In a PCR, the reaction plate 101 is subjected to a temperature cycle of approximately 95° C. to 60° C. When the sample solution 51 that has been vaporized at 95° C. is cooled to approximately 60° C., dew condensation may occur in the adhesive layer 145. Droplets formed by dew condensation scatter light during fluorescent intensity measurement by the detection apparatus 23, resulting in a decrease in signal intensity. In order to prevent dew condensation, the weight member 107 may be maintained at the temperature of approximately 95° C. to 100° C. The temperature of the weight member 107 should be maintained by a method that does not interfere with the optical detection by the detection apparatus 23. Examples of such temperature maintaining method include a method by which heat is provided to the weight member 107 by radiation from a distanced heat source, and a method by which a temperature adjustment apparatus is formed such that a visible light transmissive material, such as ITO (Indium Tin Oxide), is used for a surface 107a of the weight member which is in contact with the cover 105.

Figure 9:
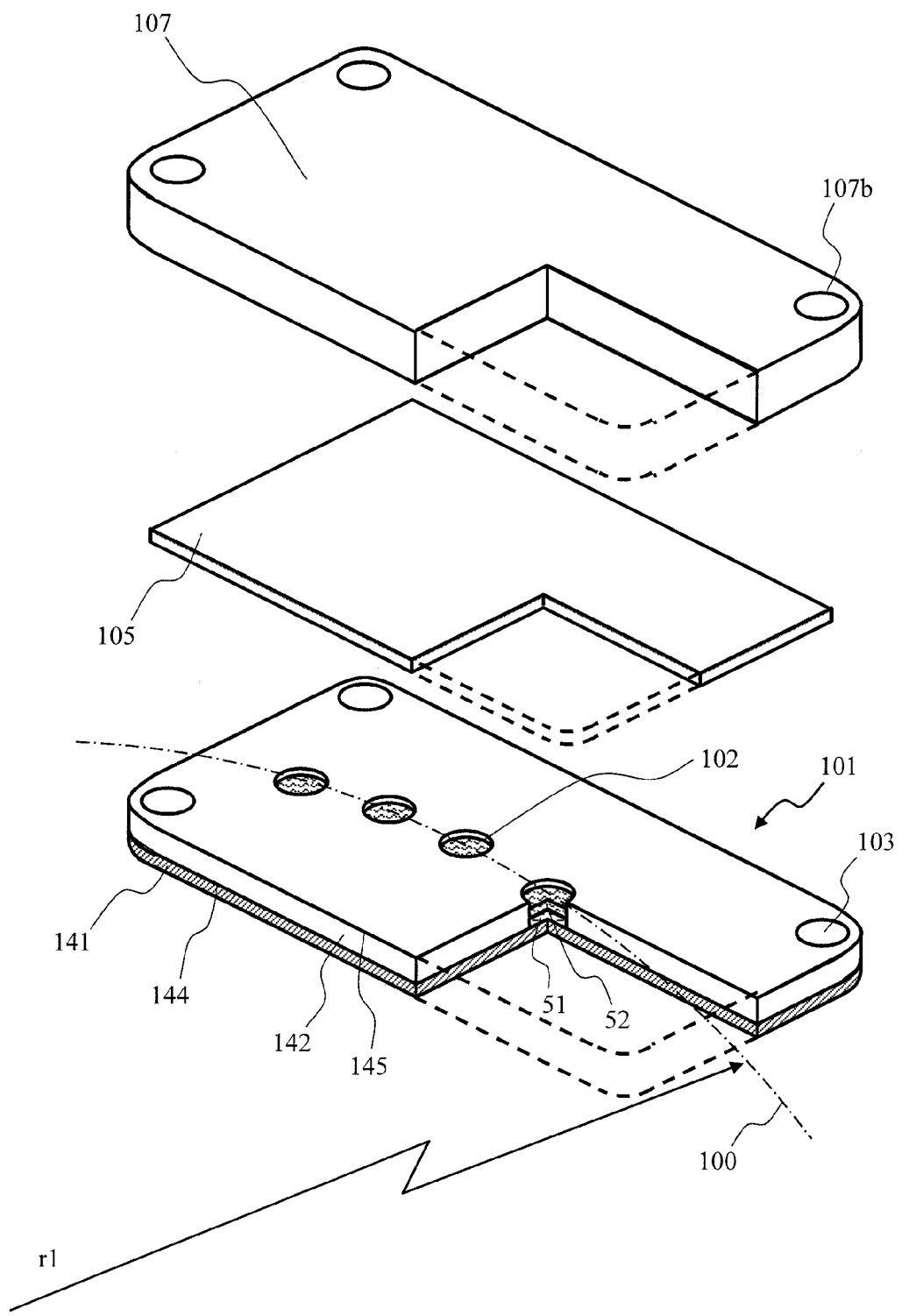
FIG. 9 is an exploded perspective view of the reaction plate assembly according to the present invention.

With reference to FIG. 9, an example of the structure of the reaction plate assembly will be described. In FIG. 9, portions indicated by broken lines are removed to show the cross sectional structure in a readily understandable manner. The reaction plate assembly includes the reaction plate 101, the transparent cover 105 placed thereon, and the weight member 107 placed thereon. The reaction plate 101 includes, from the lower surface side, the bottom plate portion 141 and the main plate portion 142. Between the bottom plate portion 141 and the main plate portion 142, and between the main plate portion 142 and the cover 105, thin adhesive layers 144 and 145, respectively, are provided.

In the ends of the reaction plate 101, the holes 103 are formed, while in the ends of the weight member 107, holes 107b are formed. The holes 103 of the reaction plate 101 are connected to the holes 107b of the weight member 107 to form reaction plate assembly holes. By inserting pins in the reaction plate assembly holes and moving the pins, the reaction plate assembly can be moved.

In the reaction plate 101, a plurality of the reaction wells 102 is formed. The reaction wells 102 are formed by the through holes in the main plate portion 142 and the upper surface of the bottom plate portion 141. In the reaction wells 102, the sample solution 51 and the oil 52 are loaded. The oil 52 is used for preventing evaporation of the sample solution 51. All of the reaction wells 102 are disposed on the circumference with the radius r1. As illustrated in FIG. 2, when the plurality of the reaction plates 101 or the reaction plate assemblies are arranged on the temperature adjustment apparatuses along the circumferential direction, all of reaction wells are disposed on the same circumference. Thus, when the reaction plates 101 or the reaction plate assemblies are rotated by the rotation drive apparatus, all of the reaction wells pass immediately under the detection apparatus 23. Accordingly, the samples in all of the reaction wells can be detected without moving the detection apparatus 23.

In the illustrated example, the size of the cover 105 in the longitudinal direction thereof is smaller than the size of the reaction plate 101 in the longitudinal direction thereof. However, the size of the cover 105 in the longitudinal direction thereof may be the same as the size of the reaction plate 101 in the longitudinal direction thereof. In such a case, the cover 105 may also need to be provided with holes.

In the nucleic acid analysis apparatus described with reference to FIGS. 2 and 3, the reaction plate assemblies may be loaded, or the reaction plates 101 may be loaded.

As described with reference to FIGS. 2 and 3, in the nucleic acid analysis apparatus according to the present invention, as many reaction plate assemblies or reaction plates as necessary may be mounted, and PCR is performed by rotating the reaction plate assemblies or reaction plates over and in contact with the temperature adjustment apparatuses set for a plurality of temperatures. When the reaction wells 102 pass under the detection apparatus 23, fluorescent intensity is measured. Even when there is a reaction plate assembly or reaction plate 101 for which measurement has already been started, the reaction plate assemblies or the reaction plates 101 can be inserted successively when there is vacancy on the temperature adjustment apparatuses. The reaction plate assemblies or the reaction plates 101 that have been measured can be successively ejected.

Thus, by using the reaction plates 101 according to the present invention, fluorescent intensity measurement can be performed for all of the reaction wells while the optics are fixed, so that a high speed PCR apparatus that can consecutively load/unload a plurality of the reaction plates 101 can be provided.

Figure 10:
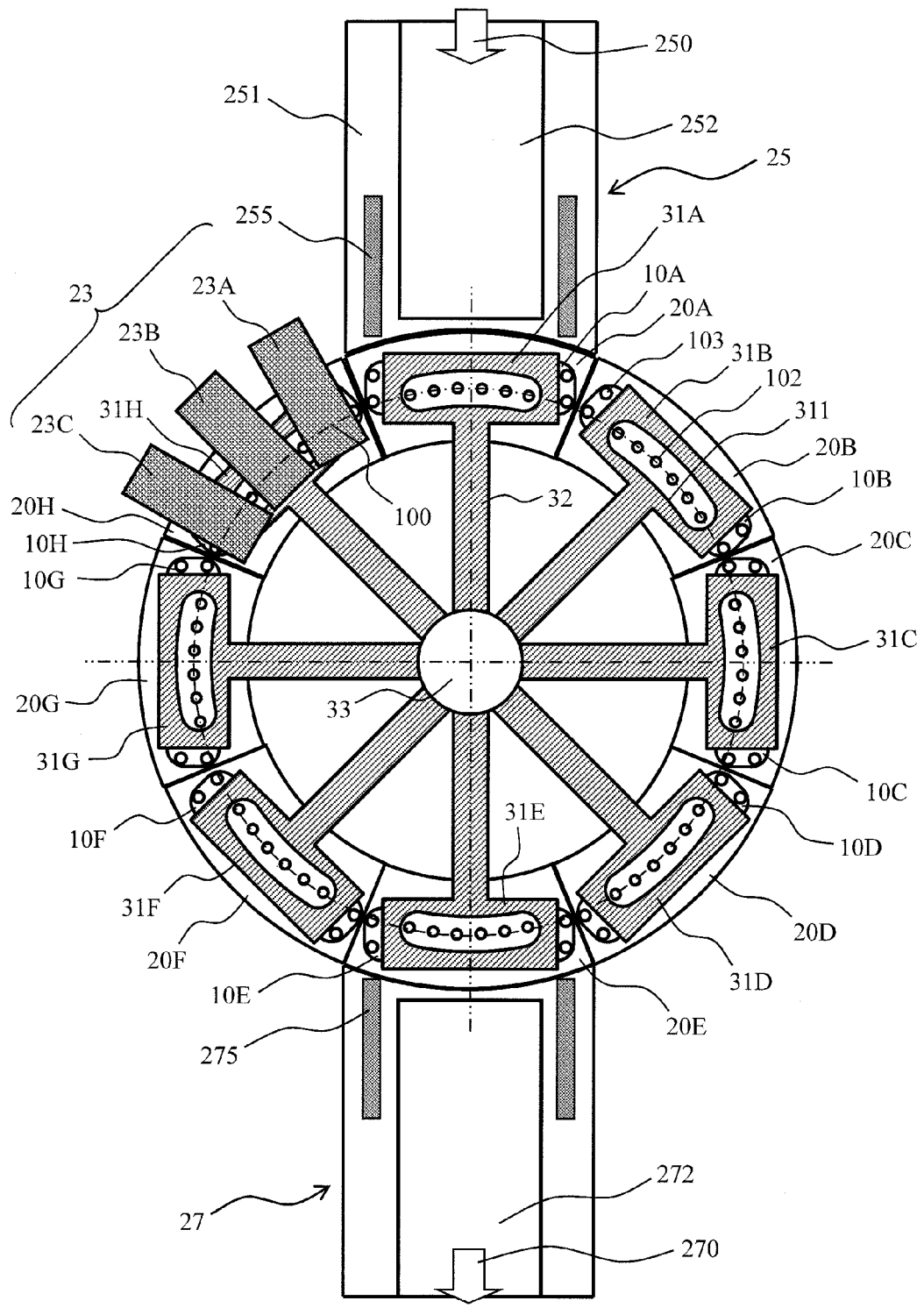
FIG. 10 illustrates a planar configuration of a major portion of the nucleic acid analysis apparatus according to the present invention.

With reference to FIG. 10, the nucleic acid analysis apparatus according to the present invention will be described. FIG. 10 illustrates the planar configuration of a major portion of the nucleic acid analysis apparatus. The nucleic acid analysis apparatus according to the present example includes the first to the eighth temperature adjustment apparatuses 20A to 20H disposed along the circumferential direction; detection apparatuses 23A to 23C disposed over the eighth temperature adjustment apparatus 20H; a delivery base 25 disposed on the outer peripheral side of the first temperature adjustment apparatus 20A; and an ejection base 27 disposed on the outer peripheral side of the fifth temperature adjustment apparatus 20E.

The number of the reaction plate assemblies 10A to 10H that are loaded over the temperature adjustment apparatuses 20A to 20H may be the same as, greater than, or smaller than the number of the temperature adjustment apparatuses 20A to 20H. The reaction plate assemblies 10A to 10H include the reaction plates and the transparent weight members disposed thereon. The reaction plates include the reaction wells 102 and the holes 103. The weight members also have holes at positions corresponding to the holes 103 in the reaction plates. The holes of the weight members and the holes 103 of the reaction plates are connected to form the guide pin holes of the reaction plate assemblies. The structure of the reaction plates will be described later with reference to FIGS. 12A to 12E. The reaction plates and the weight members are formed from a material with high heat conductivity.

The reaction wells 102 are charged with a nucleic acid and a required reagent. On the upper surface of the reaction plates, a thin transparent cover of a resin is attached to cover the reaction wells. The reaction wells are sealed by the transparent covers. The weight member is disposed on the transparent cover attached to the upper surface of the reaction plate. The weight member prevents the peeling of the transparent cover.

The nucleic acid analysis apparatus according to the present example further includes a rotating mechanism that rotates the reaction plate assemblies 10A to 10H over the temperature adjustment apparatuses 20A to 20H along the circumferential direction at a constant speed. The reaction plate assemblies 10A to 10H slide over the temperature adjustment apparatuses 20A to 20H in thermal contact with the temperature adjustment apparatuses 20A to 20H.

The rotating mechanism includes a rotating shaft 33, a support member 32 connected to the rotating shaft, and pressing portions 31A to 31H supported by the support member 32. The pressing portions 31A to 31H are configured to press the reaction plate assemblies 10A to 10H onto the temperature adjustment apparatuses 20A to 20H. The pressing portions 31A to 31H have windows 311. Through the windows 311, the reaction wells 102 of the reaction plates can be observed. An example of the structure of the pressing portions 31A to 31H will be described later with reference to FIG. 13.

According to the present example, the rotating mechanism includes the eight pressing portions 31A to 31H. However, the rotating mechanism may have a different structure as long as the structure enables the pressing of the reaction plate assemblies 10A to 10H onto the temperature adjustment apparatuses 20A to 20H. For example, while the support member 32 is a spoke-like member attached to the rotating shaft 33, the support member 32 may have a different structure.

The rotating shaft 33 is rotated by a motor at a constant speed. As the rotating shaft 33 rotates, the reaction plate assemblies 10A to 10H being pressed down by the pressing portions 31A to 31H are also rotated, together with the pressing portions 31A to 31H. The reaction plate assemblies 10A to 10H are moved along the circumferential direction relative to the temperature adjustment apparatuses 20A to 20H. During the movement of the reaction plate assemblies 10A to 10H, the reaction plates are maintained at a predetermined temperature by the temperature adjustment apparatuses 20A to 20H.

The nucleic acid analysis apparatus according to the present example is further provided with a delivery drive mechanism that delivers the reaction plate assemblies from the delivery base 25 onto the first temperature adjustment apparatus 20A.

The delivery base 25 includes a pre-heating heater 251 which is a pre-heating (enzyme activation) heat source, and a pre-heating cover 252. The reaction plate assemblies may be disposed on the pre-heating heater 251. The pre-heating cover 252 is configured to cover the reaction plate assemblies disposed on the pre-heating heater 251. A distance in the height direction between the pre-heating heater 251 and the pre-heating cover 252 is substantially equal to the thickness of the reaction plate assemblies. Thus, the pre-heating cover 252 can be placed in close contact with the reaction plate assembly. Preferably, the pre-heating cover 252 is maintained at the same temperature as the temperature of the pre-heating heater 251.

The delivery drive mechanism is provided with a pair of introduction guide pin arms 255. The introduction guide pin arms 255 include guide pins (see FIG. 16A) extending downward from the introduction guide pin arms 255.

When the reaction plate assembly is delivered onto the temperature adjustment apparatus, the guide pins of the introduction guide pin arms 255 are inserted into the guide pin holes of the reaction plate assembly. Then, the introduction guide pin arms are moved radially inward (arrow 250). The two introduction guide pin arms 255 are spaced apart from each other by a distance slightly greater than the width of the pressing portions 31A to 31H. Thus, the front ends of the two introduction guide pin arms 255 are configured to be movable radially inward in such a manner as to sandwich the pressing portions 31A to 31H from both ends. As the introduction guide pin arms 255 are moved, the reaction plate assembly is moved radially inward and disposed on the first temperature adjustment apparatus 20A.

In the delivery drive mechanism according to the present example, the reaction plate assemblies can be introduced onto the temperature adjustment apparatuses without stopping the rotation of the rotating shaft 33, as will be later described with reference to FIGS. 16A to 16F.

According to the present example, the delivery drive mechanism moves the reaction plate assembly over the pre-heating heater 251 and further delivers the reaction plate assembly from the pre-heating heater 251 to the first temperature adjustment apparatus 20A. However, the delivery drive mechanism may be configured to only deliver the reaction plate assembly from the pre-heating heater 251 to the first temperature adjustment apparatus 20A, and the movement of the reaction plate assembly over the pre-heating heater 251 may be performed by a separate drive mechanism.

The nucleic acid analysis apparatus according to the present example is further provided with an ejection drive mechanism that ejects the reaction plate assembly from the fifth temperature adjustment apparatus 20E onto the ejection base 27.

The ejection base 27 is provided with a cover 272. The ejection drive mechanism is provided with a pair of ejection guide pin arms 275. The ejection guide pin arms 275 have guide pins (not illustrated) which extend downward from the ejection guide pin arms 275.

When the reaction plate assembly is ejected from the temperature adjustment apparatus, the ejection guide pin arms 275 are moved radially inward. The two ejection guide pin arms 275 are spaced apart from each other by a distance slightly greater than the width of the pressing portions 31A to 31H. Thus, the front ends of the two ejection guide pin arms 275 can be moved radially inward in such a manner as to sandwich the pressing portions 31A to 31H from both ends. Next, the guide pins of the ejection guide pin arms 275 are inserted into the guide pin holes of the reaction plate assembly disposed on the fifth temperature adjustment apparatus 20E. Then, the ejection guide pin arms 275 are moved radially outward (arrow 270). As the ejection guide pin arms 275 are moved, the reaction plate assembly is moved radially outward and disposed on the ejection base 27.

In the ejection drive mechanism according to the present example, the reaction plate assembly can be ejected from the temperature adjustment apparatus without stopping the rotation of the rotating shaft 33.

The detection apparatuses 23A to 23C are disposed above the eighth temperature adjustment apparatus 20H. The detection apparatuses 23A to 23C may be optical detection apparatuses that irradiate the sample placed in the reaction wells 102 with excitation light, and measure the intensity of fluorescence from the sample placed in the reaction wells 102. The detection apparatuses 23A to 23C respectively detect emission from different dyes. In the illustrated example, three detection apparatuses are provided, so that emission from three kinds of dye can be detected.

When the reaction plate assemblies slide over the eighth temperature adjustment apparatus 20H, the reaction wells of the reaction plate assemblies pass immediately under the detection apparatuses 23A to 23C. The reaction wells 102 are arranged in an arc shape on the reaction plates. The reaction plate assemblies are disposed over the temperature adjustment apparatuses such that the reaction wells 102 are disposed along the circumference of a circle about the center of rotation of the rotating shaft 33. Thus, when the reaction plate assemblies are moved over the temperature adjustment apparatuses along the circumferential direction, all of the reaction wells are moved along the same circumference.

An operation of the nucleic acid analysis apparatus according to the present example will be described. While the nucleic acid analysis apparatus can perform various analyses, a case in which PCR is performed will be described. A nucleic acid extracted from a blood or tissue sample, and a reagent (such as enzyme, primer, or buffer) required for PCR reaction are dispensed into the reaction wells in the reaction plate. The reaction wells are sealed with the transparent cover, and the transparent weight member is disposed thereon, thus forming the reaction plate assemblies 10A to 10H.

In the delivery base 25, pre-heating (enzyme activation) is performed. The pre-heating heater 251 maintains the reaction plate assemblies at 95° C. Preferably, the pre-heating cover 252 is also maintained at the temperature of 95° C. The reaction plate assemblies are held on the pre-heating heater 251 for about 10 minutes. These temperature and time are necessary for activating an enzyme added in the reaction wells in the case where the extracted nucleic acid is DNA.

When RNA is extracted, a reverse transcription step in which the temperature is maintained at 40° C. for five minutes is required immediately before pre-heating (enzyme activation). In this case, a 40° C. pre-heating heater (not illustrated), a pre-heating cover (not illustrated), and guide pins (not illustrated) may be added in a stage prior to the illustrated delivery base 25.

When pre-heating (enzyme activation) is completed on the delivery base 25, the reaction plate assembly is delivered by the delivery drive mechanism from the delivery base 25 onto the first temperature adjustment apparatus 20A. The delivery drive mechanism delivers the reaction plate assembly onto the first temperature adjustment apparatus 20A without stopping the rotation of the rotating shaft 33. The reaction plate assembly slides over the temperature adjustment apparatuses 20A to 20H sequentially in thermal contact with the temperature adjustment apparatuses 20A to 20H. The temperature of the first to the eighth temperature adjustment apparatuses 20A to 20H is set in accordance with a predetermined temperature cycle. Namely, the nucleic acid retained in the reaction wells of the reaction plate is subjected to the temperature cycle determined by the first to the eighth temperature adjustment apparatuses 20A to 20H.

During PCR, a temperature cycle including a step of thermally denaturing a nucleic acid by heating a solution of the nucleic acid and an amplifying reagent to approximately 95° C., and a step of annealing and elongation of the nucleic acid by cooling to a temperature of approximately 60° C. is used. The temperature cycle is normally repeated 30 to 40 times.

Here, the temperature cycle is assumed to be completed when the reaction plate assembly makes one rotation. When the temperature cycle is repeated 30 to 40 times, the reaction plate assembly is rotated 30 to 40 times. The temperature for the first to the eighth temperature adjustment apparatuses 20A to 20H is set as follows, for example.

First temperature adjustment apparatus 20A: 95° C.
Second temperature adjustment apparatus 20B: 95° C.
Third temperature adjustment apparatus 20C: 60° C.
Fourth temperature adjustment apparatus 20D: 60° C.
Fifth temperature adjustment apparatus 20E: 60° C.
Sixth temperature adjustment apparatus 20F: 60° C.
Seventh temperature adjustment apparatus 20G: 60° C.
Eighth temperature adjustment apparatus 20H: 60° C.

The time (period) of the temperature cycle is 50 to 200 seconds, such as 100 to 150 seconds. The time of the temperature cycle may be determined by PCR assay and reagent. When a reagent that allows for high speed reaction is used, the time of the temperature cycle may be shortened so that the nucleic acid analysis time can be decreased. Further, the time of the temperature cycle may be varied by the material and structure of the reaction plate assemblies. By using a material with high heat conductivity as the material for the reaction plate assemblies and increasing the heat transfer rate between the reaction plate assemblies and the temperature adjustment apparatuses, the efficiency of the nucleic acid analysis can be increased and the nucleic acid analysis time can be decreased.

The eight temperature adjustment apparatuses may have the same size in the circumferential direction. In the present example, the two temperature adjustment apparatuses for 95° C. have a size corresponding to ¼ of the circumference. The six temperature adjustment apparatuses for 60° C. have a size corresponding to ¾ of the circumference. When the time for a single rotation of the rotating shaft 33 is t seconds, the time in which each reaction well stays in the temperature adjustment apparatuses for 95° C. is (¼)t seconds, while the time in which each reaction well stays in the temperature adjustment apparatuses for 60° C. is (¾)t seconds. The time in which each reaction well stays in the temperature adjustment apparatuses for 95° C. or the temperature adjustment apparatuses for 60° C. is set in advance. By varying the rotating speed of the rotating shaft 33, the time in which each reaction well stays in the temperature adjustment apparatuses for 95° C. or the temperature adjustment apparatuses for 60° C. can be set at a predetermined value.

At the end of every temperature cycle, the sample placed in the reaction wells of the reaction plate is optically observed by the detection apparatuses 23A to 23C disposed above the eighth temperature adjustment apparatus 20H. Here, because three detection apparatuses are provided, emission from three kinds of dye can be detected.

After the temperature cycle is repeated a predetermined number of times, the reaction plate assembly is ejected from the fifth temperature adjustment apparatus 20E onto the ejection base 27 by the ejection drive mechanism.

In the nucleic acid analysis apparatus according to the present example, there is no need to start or end the temperature cycle for all of the reaction plate assemblies disposed in the pressing portions 31A to 31H simultaneously. When there is a vacancy in any of the pressing portions 31A to 31H, the reaction plate assembly can be newly inserted there at any time. For example, when the reaction plate assemblies arrive at the delivery base 25 successively or as needed, the reaction plate assemblies can be placed in the vacant pressing portion successively or as needed. The reaction plate assemblies for which PCR reaction has been completed can be ejected successively or as needed. Thus, by inserting the reaction plate assemblies into all of the pressing portions 31A to 31H at all times such that no vacancy is produced, PCR can be efficiently implemented.

In the nucleic acid analysis apparatus according to the present example, the reaction plate assembly on which PCR reaction has been completed can be ejected as needed, so that there is no need to wait for completion of the PCR reaction for all of the reaction plate assemblies. Therefore, the time before the analysis result is reported can be decreased. Further, because all of the reaction plate assemblies are moved along the same circumferential trajectory, the delivery base 25, the ejection base 27, and the detection apparatuses 23A to 23C may be located at one location. Thus, throughput can be increased while an increase in the overall size of the nucleic acid analysis apparatus is suppressed.

In the above example, the temperature cycle is completed when the reaction plate assembly makes one rotation. Preferably, a plurality of temperature cycles may be completed by a single rotation of the reaction plate assembly. For example, two temperature cycles may be completed in a single rotation. In this case, the temperature of the eight temperature adjustment apparatuses is set for predetermined temperatures such that the temperature cycle is completed in a half circle.

When a plurality of temperature cycles is to be completed in a single rotation of the rotating shaft of the rotating mechanism, the rotating speed of the rotating shaft 33 may need to be decreased. For example, when the same temperature cycle is to be completed twice in a single rotation of the rotating shaft of the rotating mechanism, the rotating speed is halved. When the rotating speed is decreased, the accuracy of detection of emission by the detection apparatus may be advantageously increased.

While in the above example the eight temperature adjustment apparatuses 20A to 20H are installed on the circumference, the number of the temperature adjustment apparatuses is not limited to eight. The number of the temperature adjustment apparatuses may be more or less than eight. The circumferential size of the temperature adjustment apparatuses may or may not be the same. Namely, the temperature adjustment apparatuses may be installed by equally or unequally dividing the circumference.

In the present example, the planar size of the temperature adjustment apparatuses 20A to 20H is larger than the planar size of the reaction plate assemblies 10A to 10H. Thus, the reaction plate assemblies may have various planar sizes or shapes as long as the reaction plate assemblies can be stored in the temperature adjustment apparatuses. When only predetermined reaction plate assemblies are used, the planar size and shape of the temperature adjustment apparatuses may be the same as the planar size and shape of the reaction plate assemblies.

Because the present example includes the plurality of temperature adjustment apparatuses 20A to 20H, the temperature cycle can be easily modified. However, when a modification of the temperature cycle is not required, the plurality of temperature adjustment apparatuses 20A to 20H may not be provided. For example, when only the temperature cycle including the two set temperatures for 95° C. and 60° C. is to be implemented as described above, only the two temperature adjustment apparatuses for 95° C. and 60° C. may be provided. In this case, the circumferential size of the temperature adjustment apparatuses may be set to correspond to the time for which the reaction plate assemblies are to be maintained at the respective temperatures.

In the above example, all of the reaction plate assemblies placed on the nucleic acid analysis apparatus are subjected to the same temperature cycle. However, it is also possible to subject the reaction plate assemblies loaded on the nucleic acid analysis apparatus to mutually different temperature cycles by stopping the rotating mechanism. For example, the rotating mechanism is stopped and the temperature adjustment apparatuses 20A to 20H are individually operated by independent temperature programs in accordance with mutually different temperature cycles.

The reaction plate assemblies need to be moved to the position of the detection apparatuses 23A to 23C each time the temperature cycle is completed. Also, for delivering and ejection, the reaction plate assemblies need to be moved to the reaction plate assembly delivery base or ejection base. Thus, in this case, a mechanism for moving the detection apparatuses 23A to 23C, the delivery base, and the ejection base around the temperature adjustment apparatuses may be provided.

While the above example has been described with reference to the case in which the reaction plate assemblies are loaded on the temperature adjustment apparatuses 20A to 20H of the nucleic acid analysis apparatus, the reaction plates may be loaded on the temperature adjustment apparatuses 20A to 20H.

Figure 11A:
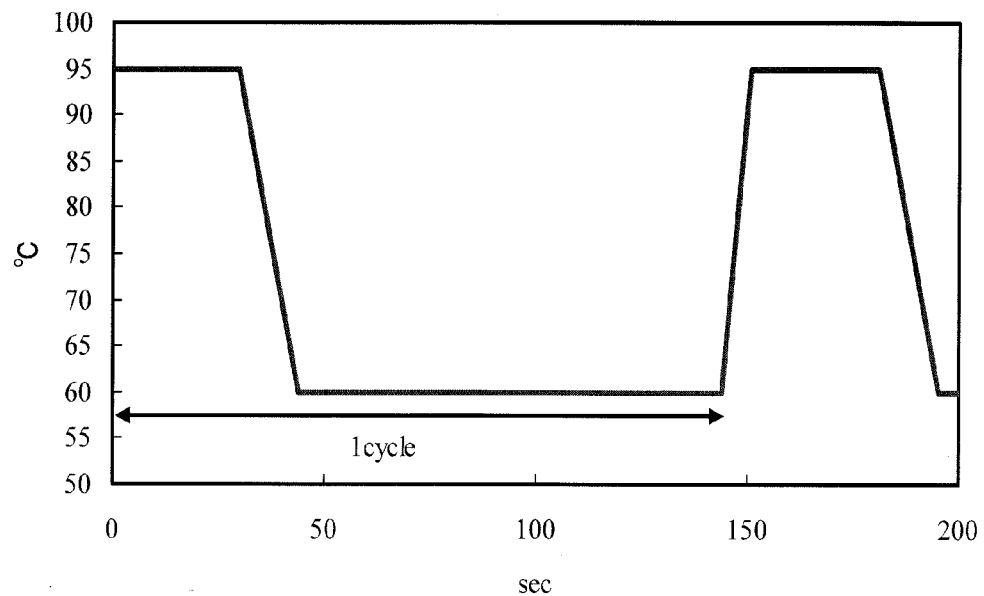
FIG. 11A illustrates an example of a temperature cycle set in a temperature adjustment apparatus of the nucleic acid analysis apparatus according to the present invention.
Figure 11B:
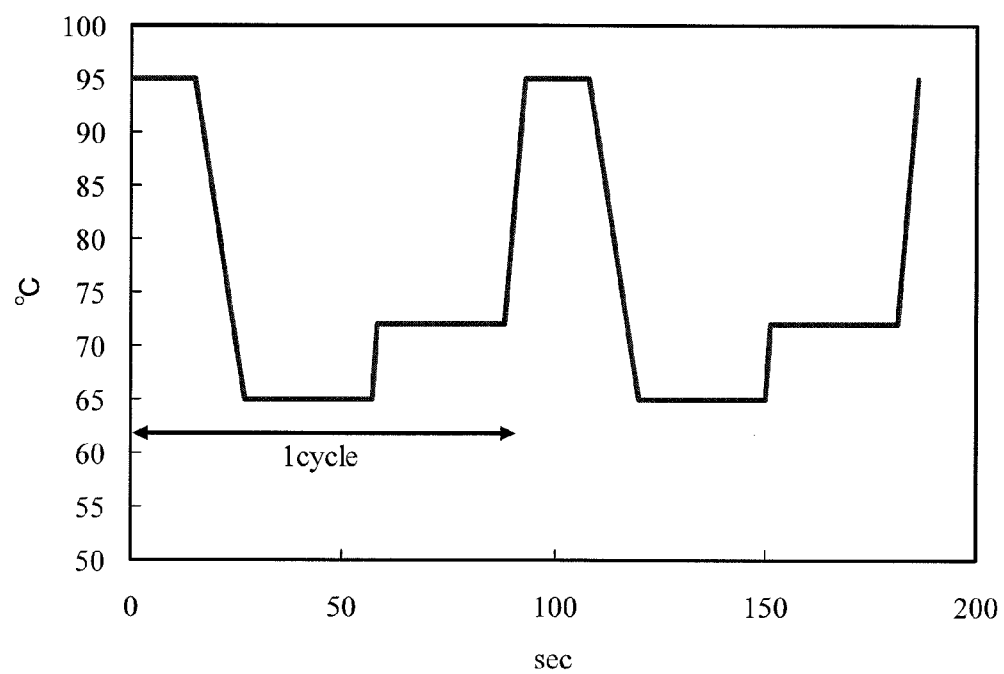
FIG. 11B illustrates an example of the temperature cycle set in the temperature adjustment apparatus of the nucleic acid analysis apparatus according to the present invention.

FIGS. 11A and 11B illustrate examples of the temperature cycle. The temperature cycle illustrated in FIG. 11A includes heating at 95° C. and retaining temperature at 60° C., as described above. The temperature cycle illustrated in FIG. 11B includes three steps of heating at 95° C., retaining temperature at 60° C., and retaining temperature at approximately 72° C. In the temperature control apparatus according to the present example, by setting the temperature of the first to the eighth temperature adjustment apparatuses 20A to 20H to predetermined temperatures, a desired temperature cycle can be implemented. Namely, in the temperature control apparatus according to the present example, by setting the temperature of each of the eight temperature adjustment apparatuses to an arbitrary temperature, an arbitrary temperature cycle can be set.

With reference to FIGS. 12A to 12E, an example of the reaction plate according to the present invention will be described. In the example illustrated in FIG. 12A, a plurality of reaction wells 102 is disposed on the upper surface of the reaction plate 101 along the circumference 100. The circumference 100 corresponds to the trajectory of the reaction wells 102 as they rotate about the rotating shaft 33. At the ends of the reaction plate 101, the guide pin holes 103 are provided.

Figure 12A:
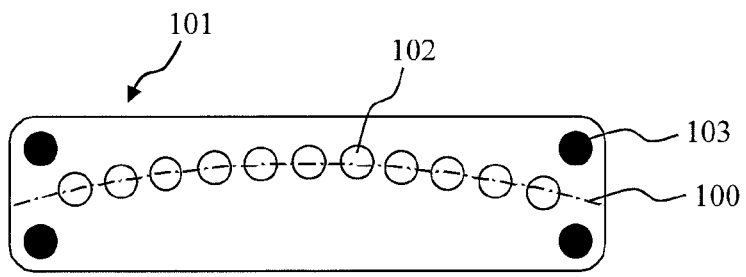
FIG. 12A illustrates an example of the reaction plate of the nucleic acid analysis apparatus according to the present invention.
Figure 12B:
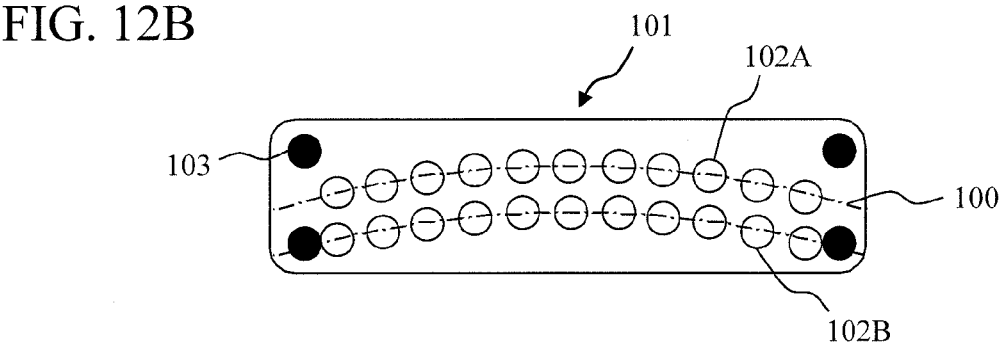
FIG. 12B illustrates an example of the reaction plate of the nucleic acid analysis apparatus according to the present invention.
Figure 12C:
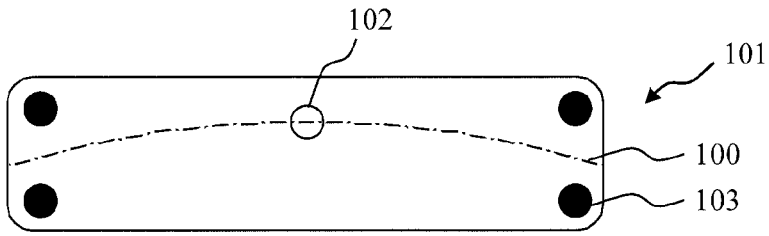
FIG. 12C illustrates an example of the reaction plate of the nucleic acid analysis apparatus according to the present invention.

In the example illustrated in FIG. 12B, two rows of reaction wells 102A and 102B are formed along concentric circles. In the present example, the detection apparatuses 23A to 23C may include two-dimensional CCD image sensors. In the example illustrated in FIG. 12C, one reaction well 102 is formed in the upper surface of the reaction plate 101.

Figure 12D:
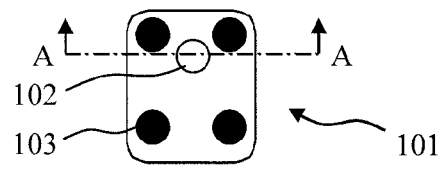
FIG. 12D illustrates an example of the reaction plate of the nucleic acid analysis apparatus according to the present invention.
Figure 12E:
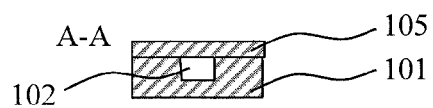
FIG. 12E illustrates a cross sectional configuration of the reaction plate of FIG. 12D.

FIGS. 12D and 12E illustrate another example of the reaction plate 101.

FIG. 12D illustrates a planar configuration of the reaction plate 101, and FIG. 12E illustrates a cross sectional configuration of the reaction plate 101 taken along line A-A of FIG. 12D. In the upper surface of the reaction plate 101, the reaction wells 102, which are recesses, are formed. After a sample and a reagent are dispensed into the reaction wells 102, the thin transparent cover 105 of resin is affixed thereon.

Figure 13:
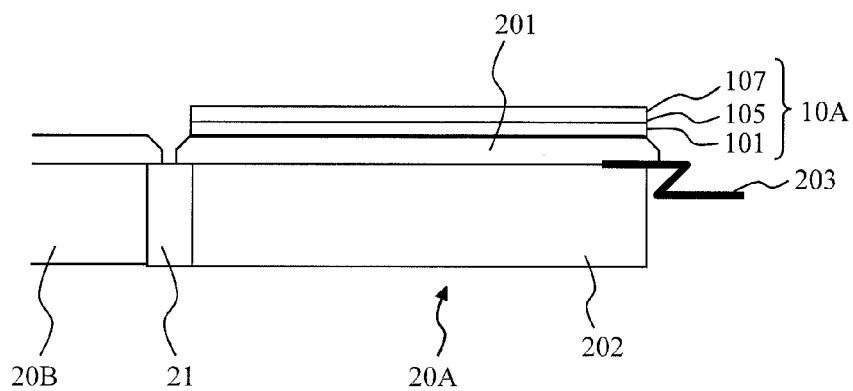
FIG. 13 illustrates a cross sectional configuration of the temperature control apparatus of the nucleic acid analysis apparatus according to the present invention.

With reference to FIG. 13, an example of the structure of the temperature adjustment apparatuses of the nucleic acid analysis apparatus according to the present invention will be described. Here, the structure of the first temperature adjustment apparatus 20A will be described. The first temperature adjustment apparatus 20A includes a heat source 202, a heat conduction plate 201 disposed thereon, and a temperature sensor 203 that detects the temperature of the heat source 202. The reaction plate assembly 10A is configured to slide over the heat conduction plate 201. The reaction plate assembly 10A includes the reaction plate 101, the transparent cover 105 disposed thereon, and the transparent weight member 107 disposed thereon.

Preferably, the heat source 202 is an electric apparatus such as a silicone rubber heater or a Peltier device. The heat conduction plate 201 is a plate-like rigid body. The heat conduction plate 201 is made from a material with high heat conductivity so that the heat from the heat source 202 can be uniformly and efficiently transmitted to the reaction plate 101. Examples of the material include metals such as aluminum, and ceramics.

The heat conduction plate 201 may be worn by the sliding of the reaction plate assembly 10A thereon. Thus, in order to prevent such wearing, the heat conduction plate 201 may be surface-treated. In the case of an aluminum plate, alumite treatment may be performed. Alternatively, at the expense of heat conductivity, a resin cover may be affixed to the heat conduction plate 201, or a thin plate of resin with high sliding property, such as POM (polyacetal, polyoxymethylene), may be closely attached thereto.

The temperature sensor 203 is mounted in contact with the heat source 202 or both the heat source 202 and the heat conduction plate 201. The temperature of the heat source 202 or the heat conduction plate 201 that is detected by the temperature sensor 203 is sent to a control unit (not illustrated) for the temperature adjustment apparatus. The control unit adjusts the value of current supplied to the heat source 202 such that the detected temperature corresponds to a predetermined temperature.

The gap between the first temperature adjustment apparatus 20A and the adjacent second temperature adjustment apparatus 20B is filled with a heat insulating material 21 so as to prevent thermal interference between the temperature adjustment apparatuses.

Figure 14:
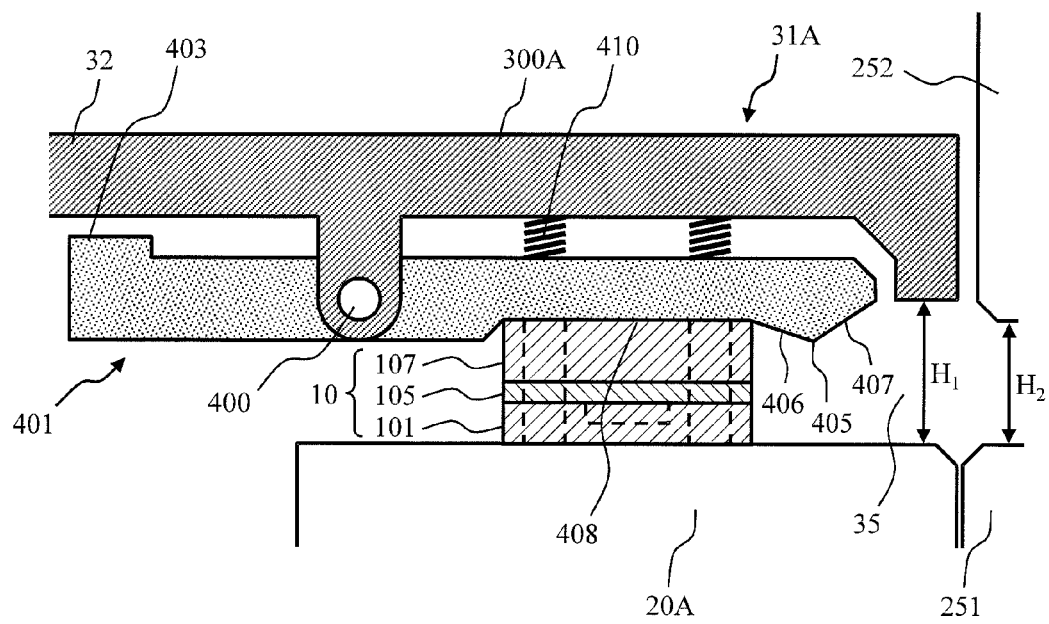
FIG. 14 illustrates a reaction plate retaining mechanism of the temperature control apparatus of the nucleic acid analysis apparatus according to the present invention.

With reference to FIG. 14, an example of the structure and operation of a reaction plate assembly retaining mechanism of the nucleic acid analysis apparatus according to the present invention will be described. The heat conduction plate 201 is not illustrated. On the first temperature adjustment apparatus 20A, the reaction plate assembly 10A is disposed. The reaction plate assembly 10A includes the reaction plate 101, the transparent cover 105 mounted thereon, and the transparent weight member 107 disposed thereon.

The heater 251 of the delivery base 25 is disposed adjacent to the temperature adjustment apparatus 20A. On the heater 251, the heater cover 252 is disposed. The distance between the temperature adjustment apparatus 20A and the heater 251 of the delivery base 25 may be so small as to be considered to be substantially in contact with each other. The upper surface of the temperature adjustment apparatus 20A and the upper surface of the heater 251 are coplanar. Between the temperature adjustment apparatus 20A and the pressing portion 31A, a delivery opening 35 for delivering the reaction plate assembly 10A is formed. The delivery opening 35 is a circumferential opening extending along the outer peripheral surfaces between the temperature adjustment apparatus 20A and the pressing portion 31A. The delivery opening 35 has a size H1 in height direction which is greater than a size H2 of the gap between the heater 251 and the heater cover 252.

The pressing portion 31A includes a pressing member 300A, a fulcrum 400, and a hook 401 pivotally mounted on the fulcrum. The hook 401 includes a protrusion 405 formed on the lower surface of the outer end of the hook 401. The protrusion 405 has tapers 406 and 407 formed on both sides. Inside the protrusion 405, a recess 408 for pressing the reaction plate assembly 10A is formed. The hook 401 also includes a protrusion 403 formed on the upper surface of the inner end of the hook 401 for controlling the stroke of the hook 401.

Between the pressing member 300A and the hook 401, springs 410 are mounted. The elastic force of the springs 410 provides the hook 401 with a pivoting force in the clockwise direction in the drawing. Thus, the hook 401 is pressed onto the reaction plate assembly 10A by the elastic force of the springs 410. The reaction plate assembly 10A is pressed onto the temperature adjustment apparatus 20A by the elastic force of the springs 410. In this way, the reaction plate 101 is closely attached to the temperature adjustment apparatus 20A, so that the temperature of the reaction plate 101 can be made exactly the same as the temperature of the temperature adjustment apparatus 20A.

The weight member 107 is used to prevent the peeling of the cover 105 affixed to the reaction plate during the temperature cycle. Thus, the weight member 107 preferably has a flat surface that can be closely attached to the cover 105 in a planar manner. Further, the weight member 107 is formed from a transparent material such that the emission from the nucleic acid in the reaction wells of the reaction plate can be optically observed. The material of the weight member 107 may be glass with a predetermined transmittance.

The weight member 107 has a predetermined heat capacity. Thus, the weight member 107 and the reaction plate 101 may not achieve a thermally uniform state, i.e., they may not have the same temperature, even when they are in contact with each other via the cover 105. For example, when the weight member 107 is in an atmosphere of room temperature and the reaction plate 101 is under the temperature condition of 95° C., a temperature difference is produced between the weight member 107 and the reaction plate 101. If vaporized sample or reagent comes into contact with the cover 105 in the reaction wells, dew condensation may be caused by cooling. In order to prevent this, the rotating mechanism is provided with a temperature adjustment mechanism. The temperature adjustment mechanism provided to the rotating mechanism may include temperature sensors and heaters installed on the hook 401 and the pressing portions 31A to 31H. The temperature sensors may be thermistors or thermocouples. The heaters may be electric resistance type heaters fed by a DC 24V power supply. The temperature adjustment mechanism provided to the rotating mechanism maintains the hook 401 and the pressing portions 31A to 31H at a predetermined temperature. While the temperature of the reaction plate 101 may be varied in accordance with the temperature set for the temperature adjustment apparatuses, the temperature of the hook 401 and the pressing portions 31A to 31H may be maintained at a constant temperature, such as 100° C.

The pressing portions 31A to 31H rotate about the rotating shaft 33. Thus, in order to control the temperature of the hook 401 and the pressing portions 31A to 31H, a structure such that the wiring from the temperature control apparatuses is not severed or entangled by the rotation is required. Accordingly, the structure around the rotating shaft will be described.

Figure 15A:
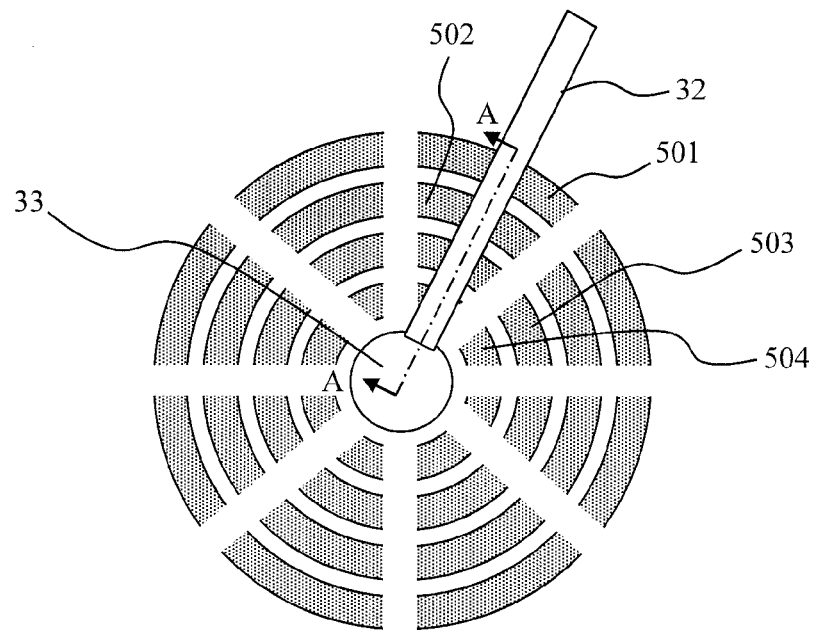
FIG. 15A illustrates a temperature adjustment wiring for a reaction plate assembly retaining mechanism of the temperature control apparatus of the nucleic acid analysis apparatus according to the present invention.
Figure 15B:
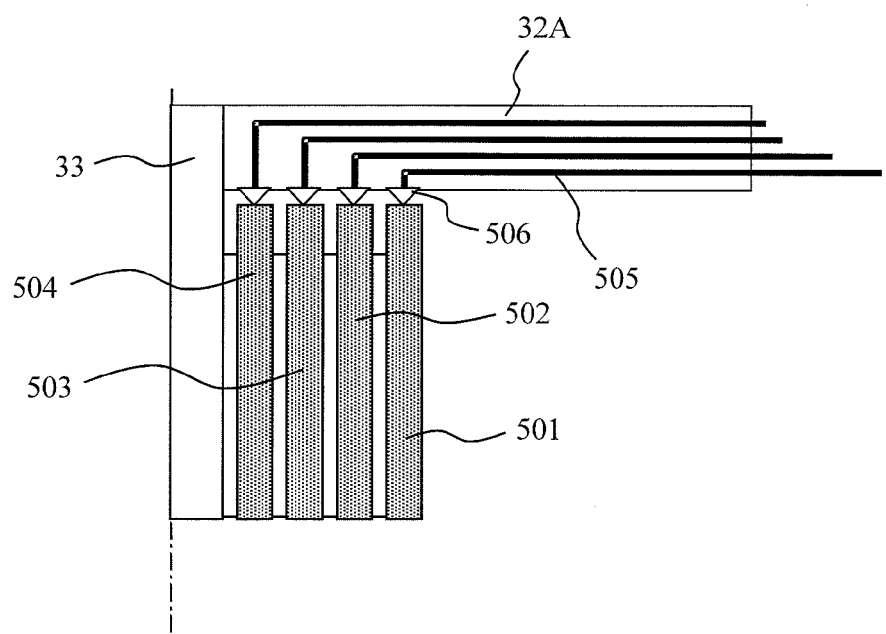
FIG. 15B illustrates the temperature adjustment wiring for the reaction plate assembly retaining mechanism of the temperature control apparatus of the nucleic acid analysis apparatus according to the present invention.

With reference to FIGS. 15A and 15B, the wiring for temperature adjustment of the retaining mechanism of the reaction plate assembly will be described. FIG. 15A illustrates a planar configuration of the rotating shaft. While the rotating shaft has eight support members attached thereto, only one support member 32 is illustrated. Around the rotating shaft 33, four electrodes 501 to 504 are disposed, the number of which corresponding to the number of wires. The four electrodes 501 to 504 are formed in an arc shape and disposed concentrically. The four electrodes 501 to 504 are divided into eight segment electrodes, the number of which corresponding to the number of the support members. The eight segment electrodes are disposed correspondingly to the eight temperature adjustment apparatuses.

FIG. 15B illustrates a cross sectional configuration taken along line A-A of FIG. 15A. In the support member 32, wires 505 are disposed. In the illustrated example, four wires 505 are disposed. At the inner end of the wires 505, sliding electrodes 506 are connected. The sliding electrodes 506 for the four wires 505 are respectively electrically connected to the four fixed electrodes 501 to 504.

For example, the two electrodes 501 and 502 on the outer peripheral side are used for the output of the temperature sensors installed on the hook 401 or the pressing portions 31A to 31H. The two electrodes 503 and 504 on the inner peripheral side may be used for supplying power to the heaters installed on the hook 401 or the pressing portions 31A to 31H, such as for DC 24V and grounding.

When the rotating shaft 33 is rotated, the support member 32 also rotates. During the rotation of the support member 32, the sliding electrodes 506 slide over and in contact with the corresponding four electrodes 501 to 504.

In the present example, the four fixed electrodes 501 to 504 are divided into the eight segment electrodes along the circumferential direction. When the support member 32 is moved from one segment electrode to the next segment electrode, the sliding electrodes of the support member 32 are not in contact with the fixed electrodes. Thus, at this time, the temperature sensors and heaters installed on the pressing portions 31A to 31H stop operating. However, because the distance between the two adjacent segment electrodes is sufficiently small, the time in which the operation of the temperature sensors and heaters installed on the pressing portions 31A to 31H is stopped is short.

When the temperature adjustment mechanism provided to the rotating mechanism is formed by a single temperature sensor and heater, the four fixed electrodes need not be divided into the eight segment electrodes. Specifically, a representative temperature of the eight hooks 401 or pressing portions 31A to 31H may be detected by the single temperature sensor, the temperature may be compared with a predetermined temperature, and the difference between them may be fed back to the heater for the hook 401 or the pressing portions 31A to 31H.

Instead of the temperature sensors provided to the hook 401 or the pressing portions 31A to 31H, the wires supplying power to the heaters may be fitted with a switch element, such as a thermostat, that is turned on or off in response to temperature. In this case, the four fixed electrodes need not be divided into the eight segment electrodes.

With reference to FIGS. 16A to 16F, an operation of the pressing portion 31A of the rotating mechanism and an operation of the delivery drive mechanism will be described.

Figure 16A:
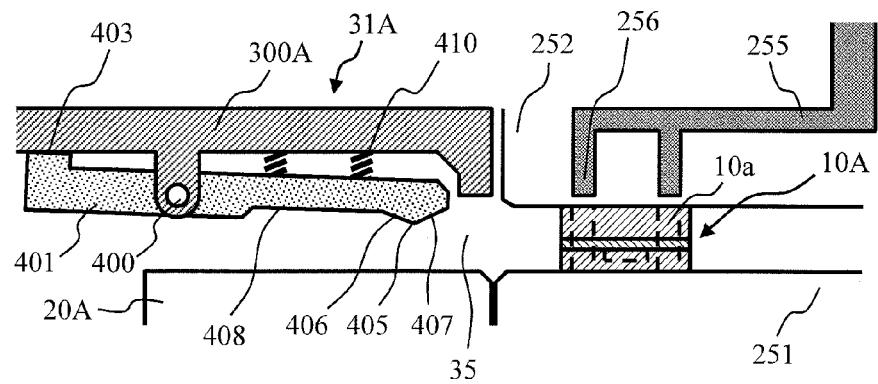
FIG. 16A illustrates an operation of a pressing portion of a rotating mechanism and a delivery drive mechanism of the nucleic acid analysis apparatus according to the present invention.

FIG. 16A illustrates a state in which the reaction plate assembly 10A is disposed on the pre-heating heater 251 of the delivery base. The upper surface of the pre-heating heater 251 and the upper surface of the first temperature adjustment apparatus 20A are coplanar. On the reaction plate assembly 10A, the pre-heating cover 252 is disposed. The delivery drive mechanism includes the guide pin arms 255 with the guide pins 256.

In order to perform pre-heating (enzyme activation), the reaction plate assembly 10A is retained on the pre-heating heater 251 at 95° C. for approximately 10 minutes.

The pressing portion 31A includes the pressing member 300A, the fulcrum 400, and the hook 401 pivotally mounted on the fulcrum 400. Between the outer end of the pressing member 300A and the first temperature adjustment apparatus 20A, the delivery opening 35 is formed.

Between the pressing member 300A and the hook 401, the springs 410 are mounted. The elastic force of the springs 410 provides the hook 401 with pivoting force in the clockwise direction in the drawing. The protrusion 403 on the upper side of the inner end of the hook 401 is abutted on the pressing member 300A so that the pivotal movement of the hook in the clockwise direction is limited up to a point. On both sides of the protrusion 405 on the lower side of the outer end of the hook 401, the tapers 406 and 407 are formed.

Figure 16B:
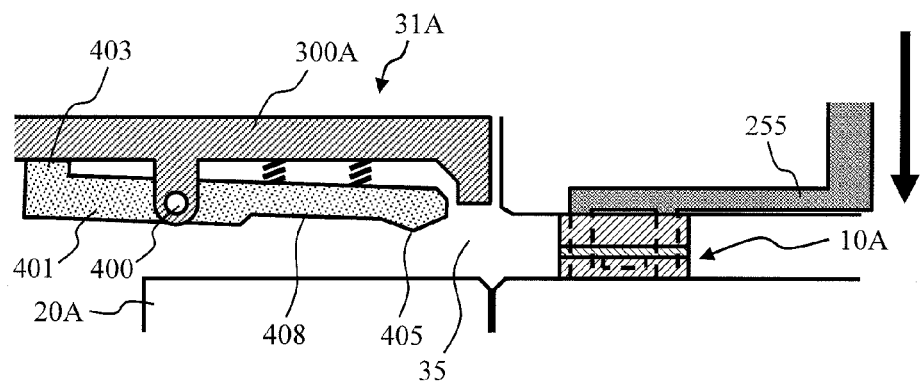
FIG. 16B illustrates the operation of the pressing portion of the rotating mechanism and the delivery drive mechanism of the nucleic acid analysis apparatus according to the present invention.

FIG. 16B illustrates a state in which the guide pins 256 have been lowered via the guide pin arms 255 connected to a drive unit. The guide pins 256 are inserted into guide pin holes 10a of the reaction plate assembly 10A. The guide pin holes 10a are formed by the weight member holes and the reaction plate holes connected to each other.

Figure 16C:
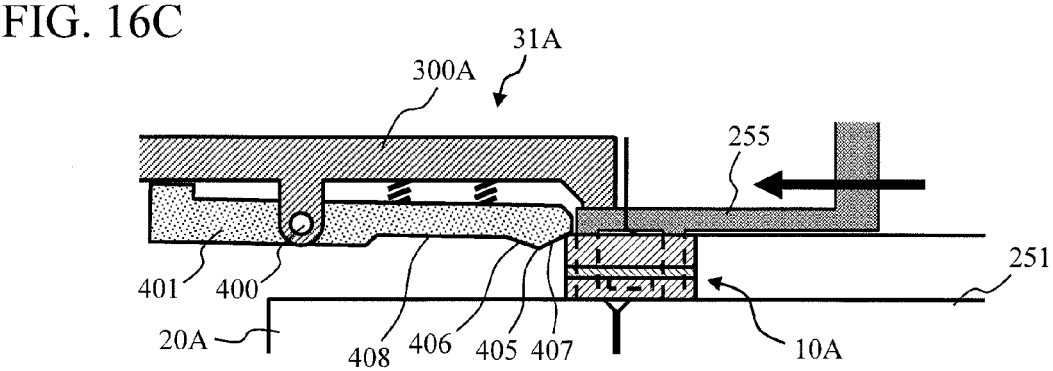
FIG. 16C illustrates the operation of the pressing portion of the rotating mechanism and the delivery drive mechanism of the nucleic acid analysis apparatus according to the present invention.

FIG. 16C illustrates a state in which the guide pin arms 255 have been moved radially inwardly of the rotating mechanism. As the guide pin arms 255 are moved radially inward, the reaction plate assembly 10A is also moved radially inward. The reaction plate assembly 10A is moved inward via the delivery opening 35. Because the upper surface of the pre-heating heater 251 and the upper surface of the first temperature adjustment apparatus 20A are coplanar, the reaction plate assembly 10A can be easily moved from the upper surface of the pre-heating heater 251 onto the upper surface of the first temperature adjustment apparatus 20A through a horizontal, radially inward movement. The speed of movement of the guide pin arms 255 is sufficiently higher than the speed of movement of the pressing portion of the rotating mechanism in the circumferential direction. Thus, the reaction plate assembly 10A can be delivered without stopping the rotation of the rotating mechanism.

When the reaction plate assembly 10A is moved radially inward, the inner edge of the reaction plate assembly 10A is abutted on the outer taper 407 of the outer end of the hook 401.

Figure 16D:
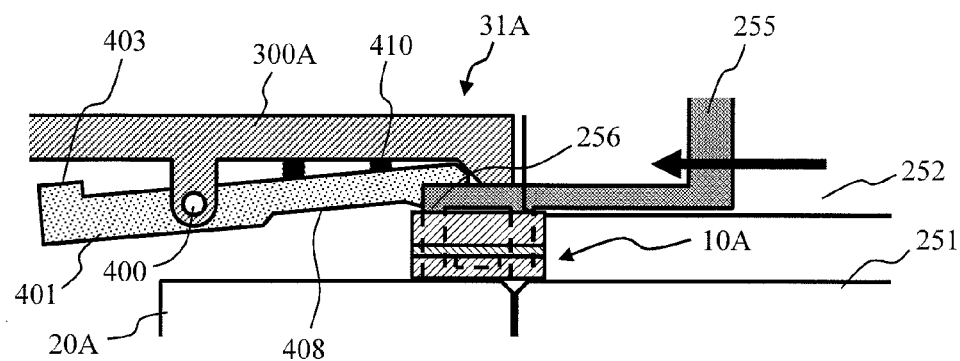
FIG. 16D illustrates the operation of the pressing portion of the rotating mechanism and the delivery drive mechanism of the nucleic acid analysis apparatus according to the present invention.

FIG. 16D illustrates a state in which the guide pin arms 255 have been further moved radially inwardly of the rotating mechanism. As the reaction plate assembly 10A is moved further radially inward, the outer end of the hook 401 is pushed up by the reaction plate assembly 10A. The hook 401 is pivotally moved about the fulcrum 400 in the anticlockwise direction in the drawing.

Figure 16E:
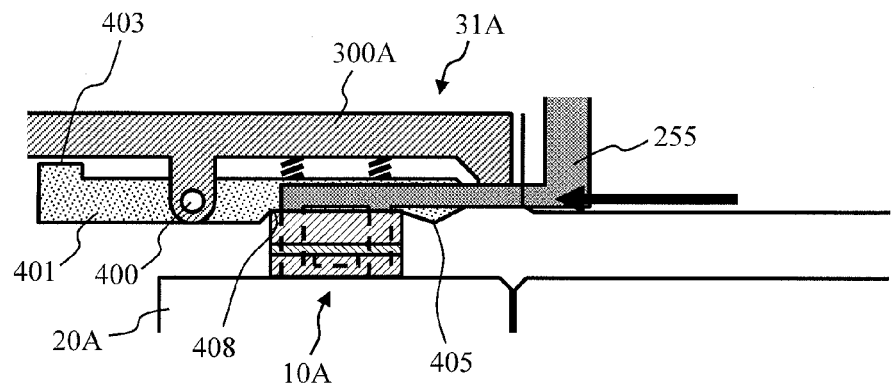
FIG. 16E illustrates the operation of the pressing portion of the rotating mechanism and the delivery drive mechanism of the nucleic acid analysis apparatus according to the present invention.

FIG. 16E illustrates a state in which the guide pin arms 255 have been further moved radially inwardly of the rotating mechanism. As the reaction plate assembly 10A is moved further radially inward, the reaction plate assembly 10A is pushed into the recess 408 of the hook 401, where the hook 401 presses the reaction plate assembly 10A by the elastic force of the springs 410. As a result, the reaction plate assembly 10A is fixed.

Figure 16F:
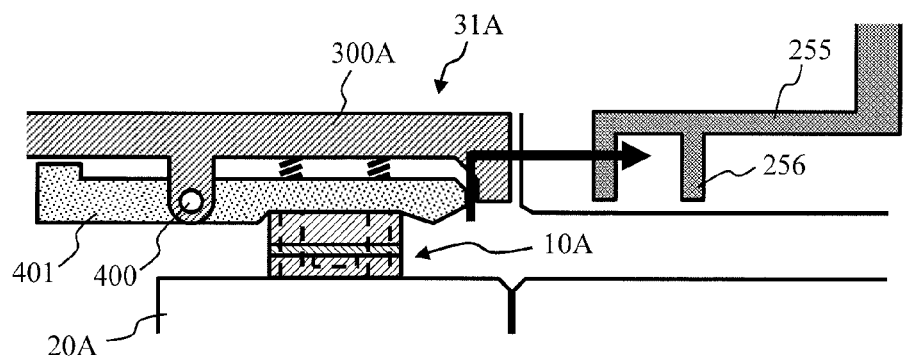
FIG. 16F illustrates the operation of the pressing portion of the rotating mechanism and the delivery drive mechanism of the nucleic acid analysis apparatus according to the present invention.

FIG. 16F illustrates a state in which the guide pin arms 255 have been lifted and moved radially outwardly of the rotating mechanism. As the guide pin arms 255 are lifted, the guide pins 256 are removed from the guide pin holes 10a of the reaction plate assembly 10A. The guide pin arms 255 are further moved radially outward and returned back to the initial position. The guide pin arms 255 then stand by for inserting the next reaction plate assembly into the next vacant pressing member.

The delivery drive mechanism may be operated only when the reaction plate assembly is disposed on the delivery base. However, the delivery drive mechanism may be operated when the reaction plate assembly is not disposed on the delivery base. The guide pin arms 255 do not collide with the pressing portion 31A or the hook 401 even when the guide pin arms 255 are blank-moved.

The operation of the ejection drive mechanism is the reversal of the operation of the delivery drive mechanism. When the reaction plate assembly is ejected from the temperature adjustment apparatus onto the ejection base by the ejection drive mechanism, an operation opposite to the above-described operation may be performed.

Figure 17:
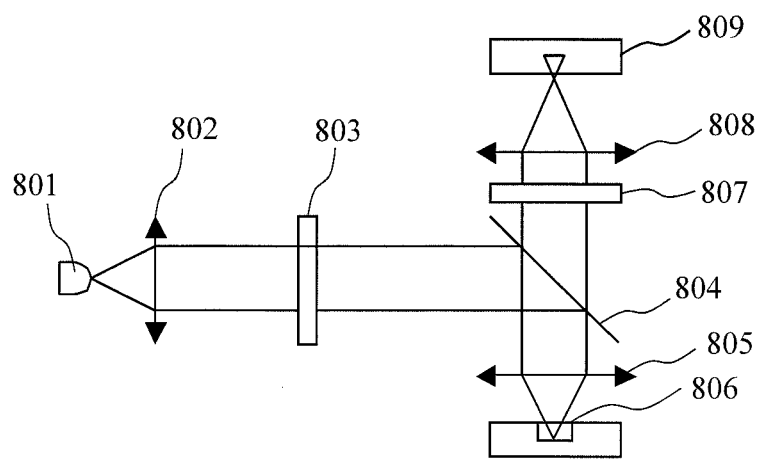
FIG. 17 illustrates a configuration of detection optics of the nucleic acid analysis apparatus according to the present invention.

With reference to FIG. 17, an example of the structure of the detection apparatus according to the present invention will be described. The detection apparatus 23 according to the present example includes a light source 801, a first lens 802, an excitation filter 803, a dichroic mirror 804, a second lens 805, a fluorescence filter 807, a third lens 808, and a detector 809.

Excitation light emitted from the light source 801 is collected by the first lens 802 to turn into parallel light. From the excitation light that has been turned into parallel light, the optimum excitation wavelength is selected by the excitation filter 803. The excitation light with the selected wavelength has its path changed by the dichroic mirror 804 and then converged by the second lens 805 before arriving at the reaction well 806. The excitation light excites the fluorescent dye in the reaction well, whereby emission is produced.

The emission (fluorescence) from the reaction well is collected by the second lens 805 into parallel light, which is transmitted through the dichroic mirror 804. From the transmitted emission, the fluorescence with a predetermined wavelength is selected by the fluorescence filter 807. The fluorescence with the selected wavelength is narrowed by the third lens 808 and then reaches the detector 809. The detector 809 detects the fluorescence.

The light source 801, which produces the excitation light for exciting the fluorescent dye in the reaction well, may be an LED or a halogen lamp. As the detector 809, a photodiode or a photo-multiplier may be used. While not illustrated, some of the excitation light that has passed through the excitation filter 803 may be split by a beam splitter for monitoring the excitation light.

The light source 801, the excitation filter 803, and the fluorescence filter 807 may be changed depending on the kind of the fluorescent dye to be detected. The nucleic acid analysis apparatus according to the present invention includes the three detection apparatuses 23A to 23C on the basis of the assumption that three kinds of fluorescent dye are used. As the detection apparatuses 23A to 23C, a CCD image sensor may be used.

Figure 18:
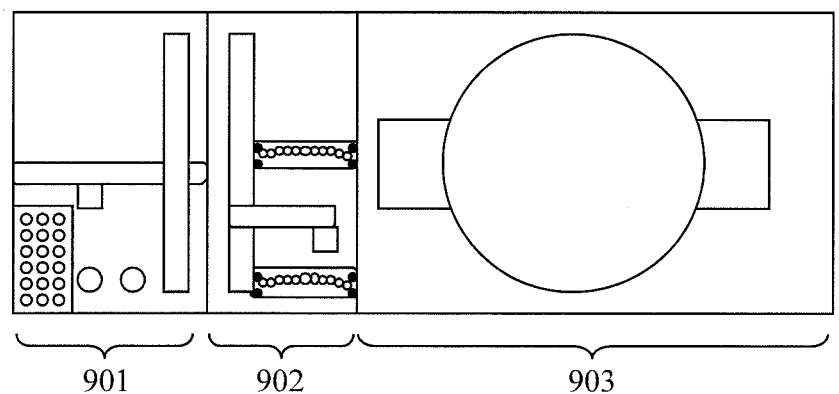
FIG. 18 illustrates an overall configuration of the nucleic acid analysis apparatus according to the present invention.

With reference to FIG. 18, an example of the nucleic acid analysis apparatus according to the present invention will be described. The nucleic acid analysis apparatus according to the present example includes a nucleic acid extraction unit 901, a dispenser unit 902, and an amplifying detection unit 903. The amplifying detection unit 903 incorporates the above-described temperature control apparatus.

The nucleic acid extraction unit 901 is a unit that extracts nucleic acid from a sample, such as whole blood or a tissue. The nucleic acid extraction unit 901 performs the following steps: (1) breaking a cell or dissolving agarose gel with a solution containing a chaotropic agent so as to elute a target nucleic acid in a buffer; (2) adding magnetic beads (magnetic silica particles) into the dissolved sample and mixing so as to cause the target nucleic acid to be adsorbed on the particle surfaces; (3) repeating B/F (solid-liquid) separation with cleaning liquid so as to remove unwanted nucleic acid or protein impurities; (4) after washing, suspending the magnetic beads in sterilized water or a low salt-concentration buffer so as to elute DNA from the bead surfaces; and (5) removing the magnetic beads from the eluate containing the target nucleic acid.

The dispenser unit 902 performs the step of dispensing the nucleic acid solution extracted by the preceding steps into the reaction wells in the reaction plate. When the analysis is directed to a single gene, for example, the nucleic acid solution from a single specimen may be dispensed into a single reaction well on the reaction plate. When the analysis is directed to a plurality of genes, the nucleic acid solution from the single specimen may be dispensed onto a plurality of reaction wells on the reaction plate. The reagent may be dispensed by the dispenser unit into the respective reaction wells, or a reaction plate that has been dispensed in advance may be provided by the manufacturer that supplies the reaction plate.

After dispensing, the transparent cover is affixed onto the upper surface of the reaction plate. The cover may be closely attached to the reaction plate thermally or by pressure. To the dispensed and sealed reaction plate, the weight member is assembled, thereby forming the reaction plate assembly.

The amplifying detection unit 903 causes a PCR reaction by using the temperature adjustment apparatus, and detects the reaction in real time.

The steps between the nucleic acid extraction unit 901 and the amplifying detection unit 903 may be divided among independent apparatuses, the amplifying detection unit and the upstream dispenser unit may be combined, or the extraction unit 901 through the amplifying detection unit 903 may form an integral apparatus.

While examples of the present invention have been described, the present invention is not limited to the foregoing examples, and it should be obvious to those skilled in the art that various modifications can be made within the scope of the invention described in the Claims.

REFERENCE SIGNS LIST 10A to 10H Reaction plate assembly
20A to 20H Temperature adjustment apparatus
21 Heat insulating material
23, 23A to 23C Detection apparatus
25 Delivery base
27 Ejection base
31A to 31H Pressing portion
32 Support member
33 Rotating shaft
35 Delivery opening
50 Communicating portion
51 Sample solution
52 Oil
100 Circumference
101 Reaction plate
101a, 101b, 101c, 101d Reaction plate boundary
101f Supposed position of reaction well
101g Intersection point of circumference and reaction plate
102, 102A, 102B Reaction well
102a Reaction well side wall
103 Guide pin hole
105 Cover
107 Weight member
107a Surface in contact with weight member cover
107b Weight member hole
141 Bottom plate portion
142 Main plate portion
144, 145 Adhesive layer
201 Heat conduction plate
202 Heat source
203 Temperature sensor
251 Pre-heating heater
252 Pre-heating cover
255 Introduction guide pin arm
256 Pin
272 Cover
275 Ejection guide pin arm
400 Fulcrum
401 Hook
405 Protrusion
406, 407 Taper
410 Spring
501 to 504 Electrodes
505 Wires
506 Sliding electrode
801 Light source
802 Lens
803 Excitation filter
804 Dichroic mirror
805 Lens
807 Fluorescence filter
808 Lens
809 Detector
901 Nucleic acid extraction unit
902 Dispenser unit
903 Amplifying detection unit
d1 Interval of adjacent reaction wells
D Width of reaction plate
d2 Interval between reaction well and outer shape boundary of reaction plate 101
o Center of arc on which reaction wells are formed
r1 Radius of arc on which reaction wells are formed
r2, r3, r4 Radius of arcs forming outer shape boundary of reaction plate 101
r5 Radius of rounded portions of reaction well
t1 Thickness of bottom plate portion
t2 Thickness of main plate portion
t3 Thickness of cover
t4, t5 Thickness of adhesive layer
t6 Height of sample solution
t7 Height of oil
t8 Thickness of weight member

The invention claimed is:

1. A nucleic acid analysis apparatus comprising:
a plurality of temperature adjustment apparatuses disposed along a circumferential direction;
a rotating mechanism that rotates a reaction plate assembly disposed on the temperature adjustment apparatuses along the circumferential direction;
a delivery base and an ejection base which are each installed on an outer peripheral side of the temperature adjustment apparatuses;
a delivery drive mechanism that delivers the reaction plate assembly from the delivery base onto the temperature adjustment apparatuses;
an ejection drive mechanism that ejects the reaction plate assembly from the temperature adjustment apparatuses to the ejection base;
a detection apparatus that optically detects a sample loaded on the reaction plate assembly,
characterized in that:
the rotating mechanism includes a rotating shaft and a plurality of pressing portions that rotate around the rotating shaft;
the reaction plate assembly is configured to be moved over the temperature adjustment apparatuses along the circumferential direction in a state of being pressed onto the temperature adjustment apparatuses by the pressing portions;
the delivery drive mechanism causes the reaction plate assembly disposed on the delivery base to be moved radially inward and delivered between the pressing portions and the temperature adjustment apparatuses; and
the ejection drive mechanism is configured to cause the reaction plate assembly disposed over the temperature adjustment apparatuses to be moved radially outward and ejected from between the pressing portions and the temperature adjustment apparatuses onto the ejection base.

2. The nucleic acid analysis apparatus according to claim 1, characterized in that:
the delivery base and the temperature adjustment apparatus have coplanar upper surfaces; and
the delivery drive mechanism is configured to deliver the reaction plate assembly from the delivery base onto the temperature adjustment apparatuses by moving the reaction plate assembly radially inward in a horizontal direction.

3. The nucleic acid analysis apparatus according to claim 1, characterized in that:
the ejection base and the temperature adjustment apparatuses have coplanar upper surfaces; and
the ejection drive mechanism is configured to eject the reaction plate assembly from the temperature adjustment apparatuses to the ejection base by moving the reaction plate assembly radially outward in a horizontal direction.

4. The nucleic acid analysis apparatus according to claim 1, characterized in that:

the delivery drive mechanism includes a pair of arms movable in a radial direction with respect to the rotating shaft, and a pin mounted on the arms;

the arms are spaced apart by a distance greater than the width of the pressing portions in the circumferential direction; and the pin is configured to be inserted in a guide pin hole formed in the reaction plate assembly.

5. The nucleic acid analysis apparatus according to claim 1, characterized in that:

the ejection drive mechanism includes a pair of arms movable in a radial direction with respect to the rotating shaft, and a pin mounted on the arms;

the arms are spaced apart by a distance greater than the width of the pressing portions in the circumferential direction; and the pin is configured to be inserted into a guide pin hole formed in the reaction plate assembly.

6. The nucleic acid analysis apparatus according to claim 1, characterized in that: the pressing portions each includes a hook, a fulcrum pivotally supporting the hook, and a spring providing the hook with pivoting force; the hook has a protrusion at an outer end in a radial direction and is configured to hold the reaction plate assembly inside the protrusion.

7. The nucleic acid analysis apparatus according to claim 6, characterized in that: the protrusion has tapers on both sides thereof; and the hook is configured to be pivotally rotated on the fulcrum when the reaction plate assembly is abutted on one of the tapers.

8. The nucleic acid analysis apparatus according to claim 1, characterized in that the hook has a protrusion at an inner end thereof for controlling a stroke of a pivotal movement of the hook.

9. The nucleic acid analysis apparatus according to claim 1, characterized in that the pressing portions include a window configured to allow the sample loaded on the reaction plate assembly to be optically detected by the detection apparatus through the window.

10. The nucleic acid analysis apparatus according to claim 1, characterized in that a number of the pressing portions is the same as a number of the temperature adjustment apparatuses.

11. The nucleic acid analysis apparatus according to claim 1, characterized in that the plurality of temperature adjustment apparatuses are configured to independently adjust temperature in accordance with a predetermined temperature cycle.

12. The nucleic acid analysis apparatus according to claim 1, characterized in that the delivery base includes a pre-heater for maintaining the temperature of the reaction plate assembly at a predetermined temperature.

13. The nucleic acid analysis apparatus according to claim 1, characterized in that: a plurality of arc-shaped electrodes are disposed concentrically around the rotating shaft, each electrode divided into a plurality of segments along the circumferential direction; the pressing portions include a temperature adjusting element to which a wire is connected; and the wire has a sliding electrode connected at an inner end thereof and contacting the arc-shaped electrodes.

14. The nucleic acid analysis apparatus according to claim 1, characterized in that the reaction plate assembly includes a reaction plate with a reaction well, a transparent cover covering the reaction plate, and a transparent weight member covering the cover.

15. The nucleic acid analysis apparatus according to claim 14, characterized in that the reaction well of the reaction plate of the reaction plate assembly is disposed on the temperature adjustment apparatuses along the circumference around the rotating shaft of the rotating mechanism.

\* \* \* \* \*